(12) United States Patent  
Miller

(10) Patent No.: US 6,720,325 B2  
(45) Date of Patent: Apr. 13, 2004

(54) CCR5 ANTAGONISTS USEFUL FOR TREATING AIDS

(75) Inventor: Michael W. Miller, Westfield, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/107,940

(22) Filed: Mar. 27, 2002

(65) Prior Publication Data

US 2003/0008877 A1 Jan. 9, 2003

Related U.S. Application Data

(60) Provisional application No. 60/279,938, filed on Mar. 29, 2001.

(51) Int. Cl.$^7$ .................. A61K 31/496; A61K 31/506; C07D 401/14; C07D 409/14

(52) U.S. Cl. ............... 514/252.18; 514/252.11; 514/253.11; 514/253.13; 514/316; 544/357; 544/295; 544/364; 546/187; 546/189

(58) Field of Search .................. 544/364, 295, 544/357; 514/252.18, 253.11, 253.13, 252.11

(56) References Cited

U.S. PATENT DOCUMENTS

| | | | |
|---|---|---|---|
| 5,883,096 | A | 3/1999 | Lowe et al. |
| 5,889,006 | A | 3/1999 | Lowe et al. |
| 5,952,349 | A | 9/1999 | Asberom et al. |
| 5,977,138 | A | 11/1999 | Wang et al. |
| 6,037,352 | A | 3/2000 | Lowe et al. |
| 6,066,636 | A | 5/2000 | Kozlowski et al. |

FOREIGN PATENT DOCUMENTS

| | | |
|---|---|---|
| EP | 1 103 276 | 6/2000 |
| WO | WO 94/18192 | 8/1994 |
| WO | WO 97/16440 | 5/1997 |
| WO | WO 97/24324 | 7/1997 |
| WO | WO 99/04794 | 2/1999 |
| WO | WO 00/66558 | 11/2000 |
| WO | WO 00/66559 | 11/2000 |

OTHER PUBLICATIONS

Tagat et al, *Bioorganic & Medicinal Chemistry Letters*, 11 (2001) 2143–2146.
Vandamme et al, *Antiviral Chemistry and Chemotherapy*, 9 (1998) p. 187–203.
Connor et al, *Virology*, 206 (1995) p. 935–944.
Plater–Zyberk et al, *Immunol. Let.*, 57 (1997) p. 117–120.
Boiardi et al, *Clinical and Experimental Rheumatology*, 17, (1999) p. 419–425.
Hatano et al, *Clin. Exp. Immunol.*, 117 (1999) p. 237–243.
Raychaudhuri et al, *International J. of Immunopharmacology*, 20 (1998) p. 661–667.
Chihara et al, *J. Allergy Clin. Immunol.*, 100, 6, part 2 (1997) p. S52–S55.
Beck et al, *J. Immunol.*, 159, 6 (1997) p. 2962–2972.

*Primary Examiner*—Emily Bernhardt  
(74) *Attorney, Agent, or Firm*—Anita W. Magatti

(57) ABSTRACT

Compounds of the formula

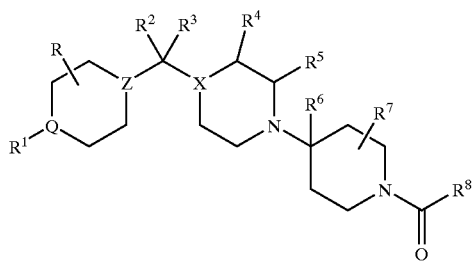

or a pharmaceutically acceptable salt or isomer thereof, wherein:

Q, X and Z are CH or N;

R, $R^4$—$R^7$ and $R^{13}$ are H or alkyl;

$R^1$ is H, alkyl, fluoroalkyl, $R^9$-arylalkyl, $R^9$-heteroarylalkyl, alkyl-$SO_2$—, cycloalkyl-$SO_2$—, fluoroalkyl-$SO_2$—, $R^9$-aryl-$SO_2$—, $R^9$-heteroaryl-$SO_2$—, $N(R^{22})(R^{23})$—$SO_2$—, alkyl-C(O)—, cycloalkyl-C(O)—, fluoroalkyl-C(O)—, $R^9$-aryl-C(O)—, NH-alkyl-C(O)— or $R^9$-aryl-NH—C(O)—;

$R^2$ is H and $R^3$ is H, alkyl, alkoxyalkyl, cycloalkyl, cycloalkylalkyl, $R^9$-aryl, $R^9$-arylalkyl, $R^9$-heteroaryl, or $R^9$-heteroarylalkyl, and when X and Z are each CH, $R^3$ is alkoxy, $R^9$-aryloxy, $R^9$-heteroaryloxy, alkylC(O)O—, alkylaminoC(O)O—, alkylC(O)$NR^{13}$—, alkylOC(O)$NR^{13}$— or alkylaminoC(O)$NR^{13}$—;

or $R^2$ and $R^3$ together are =O, =$NOR^{10}$, =N—$NR^{11}R^{12}$ or =CH-alkyl;

$R^8$ is substituted phenyl, substituted heteroaryl, naphthyl, fluorenyl, diphenymethyl, alpha-substituted benzyl or alpha-substituted heteroarylmethyl;

$R^9$—$R^{12}$ are as defined;

are disclosed for the treatment of HIV, solid organ transplant rejection, graft v. host disease, inflammatory diseases, atopic dermatitis, asthma, allergies or multiple sclerosis, as well as pharmaceutical compositions and combinations with antiviral or anti-inflammatory agents.

16 Claims, No Drawings

CCR5 ANTAGONISTS USEFUL FOR TREATING AIDS

CROSS REFERENCE TO RELATED APPLICATION

This application claims the benefit of U.S. Provisional Application No. 60/279,938, filed Mar. 29, 2001.

BACKGROUND

The present invention relates to piperidine derivatives useful as selective CCR5 antagonists, pharmaceutical compositions containing the compounds, and methods of treatment using the compounds. The invention also relates to the use of a combination of a CCR5 antagonist of this invention and one or more antiviral or other agents useful in the treatment of Human Immunodeficiency Virus (HIV). The invention further relates to the use of a CCR-5 antagonist of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis.

The global health crisis caused by HIV, the causative agent of Acquired Immunodeficiency Syndrome (AIDS), is unquestioned, and while recent advances in drug therapies have been successful in slowing the progression of AIDS, there is still a need to find a safer, more efficient, less expensive way to control the virus.

It has been reported that the CCR5 gene plays a role in resistance to HIV infection. HIV infection begins by attachment of the virus to a target cell membrane through interaction with the cellular receptor CD4 and a secondary chemokine co-receptor molecule, and proceeds by replication and dissemination of infected cells through the blood and other tissue. There are various chemokine receptors, but for macrophage-tropic HIV, believed to be the key pathogenic strain that replicates in vivo in the early stages of infection, the principal chemokine receptor required for the entry of HIV into the cell is CCR5. Therefore, interfering with the interaction between the viral receptor CCR5 and HIV can block HIV entry into the cell. The present invention relates to small molecules which are CCR5 antagonists.

CCR-5 receptors have been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

Piperidine derivatives which are muscarinic antagonists useful in the treatment of cognitive disorders such as Alzheimer's disease are disclosed in U.S. Pat. Nos. 5,883,096; 6,037,352; 5,889,006; 5,952,349; and 5,977,138.

Piperidine and piperazine derivatives useful in the treatment of AIDS are disclosed in WO 00/66559 and WO 00/66558.

A-M. Vandamme et al., *Antiviral Chemistry & Chemotherapy*, 9: 187–203 (1998) disclose current clinical treatments of HIV-1 infections in man including at least triple drug combinations or so-called Highly Active Antiretroviral Therapy ("HAART"); HAART involves various combinations of nucleoside reverse transcriptase inhibitors ("NRTI"), non-nucleoside reverse transcriptase inhibitors ("NNRTI") and HIV protease inhibitors ("PI"). In compliant drug-naive patients, HAART is effective in reducing mortality and progression of HIV-1 to AIDS. However, these multidrug therapies do not eliminate HIV-1 and long-term treatment usually results in multidrug resistance. Development of new drug therapies to provide better HIV-1 treatment remains a priority.

SUMMARY OF THE INVENTION

The present invention relates to compounds useful as CCR5 antagonist represented by the structural formula I

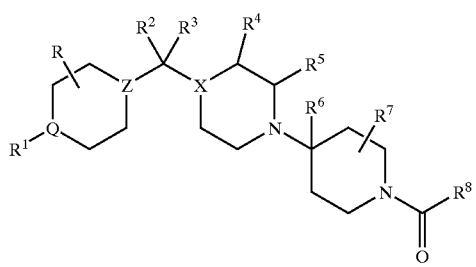

or a pharmaceutically acceptable salt or isomer thereof, wherein:

Q, X and Z are independently selected from the group consisting of CH and N, provided that one or both of Q and Z is N;

R, $R^4$, $R^5$, $R^6$ and $R^7$ are independently selected from the group consisting of H and $(C_1–C_6)$alkyl;

$R^1$ is H, $(C_1–C_6)$alkyl, fluoro-$(C_1–C_6)$alkyl-, $R^9$-aryl $(C_1–C_6)$alkyl-, $R^9$-heteroaryl-$(C_1–C_6)$alkyl-, $(C_1–C_6)$alkyl-$SO_2$—, $(C_3–C_6)$cycloalkyl-$SO_2$—, fluoro-$(C_1–C_6)$alkyl-$SO_2$—, $R^9$-aryl-$SO_2$—, $R^9$-heteroaryl-$SO_2$—, $N(R^{22})(R^{23})$—$SO_2$—, $(C_1–C_6)$alkyl-C(O)—, $(C_3–C_6)$cyclo-alkyl-C(O)—, fluoro-$(C_1–C_6)$alkyl-C(O)—, $R^9$-aryl-C(O)—, NH—$(C_1–C_6)$alkyl-C(O)— or $R^9$-aryl-NH—C(O)—;

$R^2$ is H or $(C_1–C_6)$alkyl, and $R^3$ is H, $(C_1–C_6)$alkyl, $(C_1–C_6)$alkoxy$(C_1–C_6)$alkyl-, $(C_3–C_{10})$-cycloalkyl-, $(C_3–C_{10})$cycloalkyl$(C_1–_6)$alkyl-, $R^9$-aryl, $R^9$-aryl$(C_1 – C_6)$-alkyl-, $R^9$-heteroaryl, or $R^9$-heteroaryl$(C_1–C_6)$ alkyl-, provided that both X and Z are not each N;

or $R^2$ and $R^3$ together are =O, =$NOR^{10}$, =N—$NR^{11}R^{12}$ or =CH$(C_1–C_6)$alkyl, provided that when one or both of X and Z is N, $R^2$ and $R^3$ together are not =CH $(C_1–C_6)$alkyl;

and when X and Z are each CH, $R^3$ can also be $(C_1–C_6)$ alkoxy, $R^9$-aryloxy, $R^9$-heteroaryloxy, $(C_1–C_6)$alkyl-C (O)O—, $(C_1–C_6)$alkyl-NH—C(O)O—, N($(C_1–C_6)$ alkyl)$_2$—C(O)O—, $(C_1–C_6)$alkyl-C(O)—$NR^{13}$—, $(C_1–C_6)$alkyl-O—C(O)—$NR^{13}$—, $(C_1–C_6)$alkyl-NH—C(O)—$NR^{13}$—, or N($(C_1–C_6)$alkyl)$_2$—C(O)—$NR^{13}$—;

$R^8$ is $(R^{14},R^{15},R^{16})$-substituted phenyl, $(R^{14},R^{15},R^{16})$-substituted 6-membered heteroaryl, $(R^{14},R^{15},R^{16})$-substituted 6-membered heteroaryl N-oxide, $(R^{17},R^{18})$-substituted 5-membered heteroaryl, naphthyl, fluorenyl, diphenylmethyl,

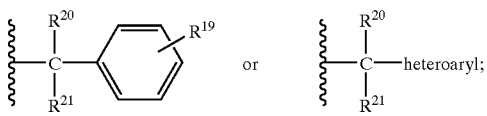

R[9] is 1, 2 or 3 substituents independently selected from the group consisting of H, halogen, $(C_1-C_6)$alkyl, $(C_1-C_6)$alkoxy, —$CF_3$, —$OCF_3$, $CH_3C(O)$—, —CN, $CH_3SO_2$—, $CF_3SO_2$— and —$N(R^{22})(R^{23})$;

R[10] is H, $(C_1-C_6)$alkyl, fluoro$(C_1-C_6)$alkyl-, $(C_3-C_{10})$cycloalkyl$(C_1-C_6)$alkyl-, hydroxy$(C_2-C_6)$alkyl-, $(C_1-C_6)$alkyl-O—$(C_2-C_6)$alkyl-, $(C_1-C_6)$alkyl-O—C(O)—$(C_1-C_6)$alkyl- or $N(R^{22})(R^{23})$—C(O)—$(C_1-C_6)$alkyl-;

R[11] and R[12] are independently selected from the group consisting of H, $(C_1-C_6)$alkyl and $(C_3-C_{10})$cycloalkyl, or R[11] and R[12] together are $C_2-C_6$ alkylene and form a ring with the nitrogen to which they are attached;

R[14] and R[15] are independently selected from the group consisting of $(C_1-C_6)$alkyl, halogen, —$NR^{22}R^{23}$, —OH, —$CF_3$, —$OCH_3$, —O-acyl and —$OCF_3$;

R[16] is R[14], hydrogen, phenyl, —$NO_2$, —CN, —$CH_2F$, —$CHF_2$, —CHO, —CH=$NOR^{24}$, pyridyl, pyridyl N-oxide, pyrimidinyl, pyrazinyl, —$N(R^{24})$ $CONR^{25}R^{26}$, —NHCONH(chloro-$(C_1-C_6)$alkyl), —NHCONH(($C_3-C_{10}$)cycloalkyl$(C_1-C_6)$alkyl), —NHCO$(C_1-C_6)$alkyl, —$NHCOCF_3$, —$NHSO_2N(R^{22})(R^{23})$, —$NHSO_2(C_1-C_6)$alkyl, —$N(SO_2CF_3)_2$, —$NHCO_2$—$(C_1-C_6)$alkyl, $C_3-C_{10}$ cycloalkyl, —$SR^{27}$, —$SOR^{27}$, —$SO_2R^{27}$, —$SO_2NH(R^{22})$, —$OSO_2(C_1-C_6)$alkyl, —$OSO_2CF_3$, hydroxy$(C_1-C_6)$alkyl-, —CON $R^{24}R^{25}$, —$CON(CH_2CH_2OCH_3)_2$, —$OCONH(C_1-C_6)$alkyl, —$CO_2R^{24}$, —$Si(CH_3)_3$ or —$B(OC(CH_3)_2)_2$;

R[17] is $(C_1-C_6)$alkyl, —$N(R^{22})(R^{23})$ or R[19]-phenyl;

R[13], R[18], R[22], R[23], R[24], R[25] and R[26] are independently selected from the group consisting of H and $(C_1-C_6)$alkyl;

R[19] is 1, 2 or 3 substituents independently selected from the group consisting of H, $(C_1-C_6)$alkyl, —$CF_3$, —$CO_2R^{25}$, —CN, $(C_1-C_6)$alkoxy and halogen;

R[20] and R[21] are independently selected from the group consisting of H and $(C_1-C_6)$alkyl, or R[20] and R[21] together with the carbon to which they are attached form a spiro ring of 3 to 6 carbon atoms; and R[27] is $(C_1-C_6)$alkyl or phenyl.

Another aspect of the invention is a pharmaceutical composition for treatment of HIV comprising an effective amount of at least one compound of formula I in combination with a pharmaceutically acceptable carrier. Another aspect of the invention is a pharmaceutical composition for treatment of solid organ transplant rejection, graft v. host disease, arthritis, rheumatoid arthritis, inflammatory bowel disease, atopic dermatitis, psoriasis, asthma, allergies or multiple sclerosis comprising an effective amount of at least one compound of formula I in combination with a pharmaceutically acceptable carrier.

Yet another aspect of this invention is a method of treatment of HIV comprising administering to a human in need of such treatment an effective amount of at least one compound of formula I. Another aspect of the invention is a method of treatment of solid organ transplant rejection, graft v. host disease, arthritis, rheumatoid arthritis, inflammatory bowel disease, atopic dermatitis, psoriasis, asthma, allergies or multiple sclerosis comprising administering to a human in need of such treatment an effective amount of at least one compound of formula I. Also contemplated is the use of at least one compound of formula I for the preparation of a medicament for the treatment of HIV, solid organ transplant rejection, graft v. host disease, arthritis, rheumatoid arthritis, inflammatory bowel disease, atopic dermatitis, psoriasis, asthma, allergies or multiple sclerosis.

Still another aspect of this invention is the use of at least one compound of formula I of this invention in combination with one or more antiviral or other agents useful in the treatment of Human Immunodeficiency Virus for the treatment of AIDS. Still another aspect of this invention is the use of at least one compound of formula I of this invention in combination with one or more other agents useful in the treatment of solid organ transplant rejection, graft v. host disease, inflammatory bowel disease, rheumatoid arthritis or multiple sclerosis. The compound(s) of formula I and antiviral or other agents which are components of the combination can be administered in a single dosage form or they can be administered separately. Therefore, a pharmaceutical composition comprising at least one compound of formula I and one or more antiviral or other agents useful in the treatment of HIV is comtemplated, as well as a pharmaceutical composition comprising at least one compound of formula I and one or more antiviral or other agents useful in the treatment of solid organ transplant rejection, graft v. host disease, inflammatory bowel disease, rheumatoid arthritis or multiple sclerosis; a kit comprising separate dosage forms of the actives for treating HIV, solid organ transplant rejection, graft v. host disease, inflammatory bowel disease, rheumatoid arthritis or multiple sclerosis is also contemplated.

DETAILED DESCRIPTION OF THE INVENTION

Preferred are compounds of formula I wherein Z is CH, and Q and X are each N. Also preferred are compounds of formula I wherein R[1] is R[9]-aryl$(C_1-C_6)$alkyl-, R[9]-heteroaryl$(C_1-C_6)$alkyl-, $(C_1-C_6)$alkyl-$SO_2$—, $(C_3-C_6)$cycloalkyl-$SO_2$—, fluoro-$(C_1-C_6)$-alkyl-$SO_2$—, R[9]-aryl-$SO_2$—, or R[9]-aryl-NH—C(O)—. More preferably, R[1] is $(C_1-C_6)$alkyl-$SO_2$—, $(C_{13}-C_6)$cycloalkyl-$SO_2$— or R[9]-aryl-$SO_2$—. Preferably R[2] is hydrogen and R[3] is $(C_1-C_6)$alkyl, R[9]-aryl, R[9]-aryl$(C_1-C_6)$-alkyl, R[9]-heteroaryl, or R[9]-heteroaryl $(C_1-C_6)$alkyl. When R[2] comprises an arylalkyl or heteroarylalkyl group, the alkyl portion of the arylalkyl or heteroarylalkyl preferably is methyl. R, R[5] and R[7] are preferably hydrogen. R[4] is preferably $(C_1-C_6)$alkyl, more preferably methyl, when X is N; R[4] is preferably H when X is CH. R[6] is preferably —$CH_3$. R[9] is preferably H, halogen, $(C_1-C_6)$alkyl or $(C_1-C_6)$alkoxy. When R[1] or R[3] comprises an aryl or heteroaryl group, a preferred aryl group is phenyl, and preferred heteroaryl groups are thienyl, pyridyl and pyrimidyl.

In compounds of formula I, R[8] is preferably (R[14], R[15], R[16])-phenyl; (R[14], R[15], R[16])-pyridyl or an N-oxide thereof; or (R[14], R[15], R[16])-pyrimidyl. When R[8] is pyridyl, it is preferably 3- or 4-pyridyl, and when pyrimidyl, it is preferably 5-pyrimidyl. The R[14] and R[15] substituents are preferably attached to carbon ring members adjacent to the carbon joining the ring to the rest of the molecule and the R[16] substituent can be attached to any of the remaining unsubstituted carbon ring members. Thus, structures of the preferred R[8] substituents are shown as follows:

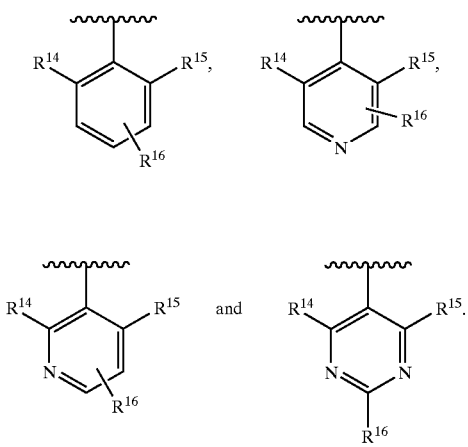

Preferred R[14] and R[15] substituents for compounds of formula I are: $(C_1-C_6)$alkyl, especially methyl; halogen, especially chloro; and —NH$_2$; a preferred R[16] substituent is hydrogen.

As used herein, the following terms are as defined below unless otherwise indicated.

Alkyl (including the alkyl portions of alkoxy, alkylamino and dialkylamino) represents straight and branched carbon chains and contains from one to six carbon atoms.

Fluoroalkyl represents an alkyl group as defined substituted by one or more fluorene atoms. Examples are —CH$_2$F, —CHF$_2$, —CF$_3$, —CH$_2$CF$_3$, —CF$_2$CF$_3$ and the like.

Hydroxyalkyl represents an alkyl group as defined substituted by 1 to 3 hydroxy groups.

Alkenyl represents $C_2-C_6$ carbon chains having one or two unsaturated bonds, provided that two unsaturated bonds are not adjacent to each other.

Substituted phenyl means that the phenyl group can be substituted at any available position on the phenyl ring.

Acyl means a radical of a carboxylic acid having the formula alkyl-C(O)—, aryl-C(O)—, aralkyl-C(O)—, $(C_3-C_7)$cycloalkyl-C(O)—, $(C_3-C_7)$cycloalkyl-$(C_1-C_6)$alkyl- C(O)—, and heteroaryl-C(O)—, wherein alkyl and heteroaryl are as defined herein.

Aryl is phenyl or naphthyl.

Heteroaryl represents cyclic aromatic groups of 5 or 6 atoms or bicyclic groups of 11 to 12 atoms having 1 or 2 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. Nitrogen atoms can form an N-oxide. For 6-membered heteroaryl rings at R[8], available carbon atoms can be substituted by R[14], R[15] or R[16] groups. All regioisomers are contemplated, e.g., 2-pyridyl, 3-pyridyl and 4-pyridyl. Typical 6-membered heteroaryl groups are pyridyl, pyrimidinyl, pyrazinyl, pyridazinyl and the N-oxides thereof. For 5-membered heteroaryl rings at R[8], available carbon atoms can be substituted by R[17] or R[18] groups. R[9]-substituted heteroaryl rings can be substituted on available carbon atoms by 1, 2 or 3 independently selected R[9] groups. Typical 5-membered heteroaryl rings are furyl, thienyl, pyrrolyl, thiazolyl, isothiazolyl, imidazolyl, pyrazolyl and isoxazolyl. 5-Membered rings having one heteroatom can be joined through the 2- or 3- position; 5-membered rings having two heteroatoms are preferably joined through the 4-position. Bicyclic groups typically are benzo-fused ring systems derived from the heteroaryl groups named above, e.g. quinolyl, phthalazinyl, quinazolinyl, benzofuranyl, benzothienyl and indolyl.

Halogen represents fluoro, chloro, bromo and iodo.

A therapeutically effective amount of a CCR5 antagonist is an amount sufficient to lower HIV-1-RNA plasma levels.

One or more, preferably one to four, antiviral agents useful in anti-HIV-1 therapy may be used in combination with at least one (i.e., 1–4, preferably 1) CCR5 antagonist compound of the present invention. The antiviral agent or agents may be combined with the CCR5 antagonist in a single dosage form, or the CCR5 antagonist and the antiviral agent or agents may be administered simultaneously or sequentially as separate dosage forms. The antiviral agents contemplated for use in combination with the compounds of the present invention comprise nucleoside and nucleotide reverse transcriptase inhibitors, non-nucleoside reverse transcriptase inhibitors, protease inhibitors and other antiviral drugs listed below not falling within these classifications. In particular, the combinations known as HAART are contemplated for use in combination with the CCR5 antagonists of this invention.

The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename from Glaxo-Wellcome Inc., Research Triangle, N.C. 27709; didanosine (ddI) available under the VIDEX tradename from Bristol-Myers Squibb Co., Princeton, N.J. 08543; zalcitabine (ddC) available under the HIVID tradename from Roche Pharmaceuticals, Nutley, N.J. 07110; stavudine (d4T) available under the ZERIT trademark from Bristol-Myers Squibb Co., Princeton, N.J. 08543; lamivudine (3TC) available under the EPIVIR tradename from Glaxo-Wellcome Research Triangle, N.C. 27709; abacavir (1592U89) disclosed in WO96/30025 and available under the ZIAGEN trademark from Glaxo-Wellcome Research Triangle, N.C. 27709; adefovir dipivoxil [bis(POM)-PMEA] available under the PREVON tradename from Gilead Sciences, Foster City, Calif. 94404; lobucavir (BMS-180194), a nucleoside reverse transcriptase inhibitor disclosed in EP-0358154 and EP-0736533 and under development by Bristol-Myers Squibb, Princeton, N.J. 08543; BCH-10652, a reverse transcriptase inhibitor (in the form of a racemic mixture of BCH-10618 and BCH-10619) under development by Biochem Pharma, Laval, Quebec H7V, 4A7, Canada; emitricitabine [(−)-FTC] licensed from Emory University under Emory Univ. U.S. Pat. No. 5,814,639 and under development by Triangle Pharmaceuticals, Durham, N.C. 27707; beta-L-FD4 (also called beta-L-D4C and named beta-L—2', 3'-dicleoxy-5-fluoro-cytidene) licensed by Yale University to Vion Pharmaceuticals, New Haven Conn. 06511; DAPD, the purine nucleoside, (−)-beta-D-2,6,-diamino-purine dioxolane disclosed in EP 0656778 and licensed by Emory University and the University of Georgia to Triangle Pharmaceuticals, Durham, N.C. 27707; and lodenosine (FddA), 9-(2,3-dideoxy-2-fluoro-b-D-threo-pentofuranosyl) adenine, an acid stable purine-based reverse transcriptase inhibitor discovered by the NIH and under development by U.S. Bioscience Inc., West Conshohoken, Pa. 19428.

The term "non-nucleoside reverse transcriptase inhibitors" ("NNRTI"s) as used herein means non-nucleosides that inhibit the activity of HIV-1 reverse transcriptase.

Typical suitable NNRTIs include nevirapine (BI-RG-587) available under the VIRAMUNE tradename from Boehringer Ingelheim, the manufacturer for Roxane Laboratories, Columbus, Ohio 43216; delaviradine (BHAP, U-90152) available under the RESCRIPTOR tradename from Pharmacia & Upjohn Co., Bridgewater N.J. 08807; efavirenz (DMP-266) a benzoxazin-2-one disclosed in WO094/03440 and available under the SUSTIVA tradename from DuPont Pharmaceutical Co., Wilmington, Del. 19880-0723; PNU-142721, a furopyridine-thio-pyrimide under development by Pharmacia and Upjohn, Bridgewater N.J. 08807; AG-1549 (formerly Shionogi # S-1153); 5-(3,5-dichlorophenyl)-thio4-isopropyl-1-(4-pyridyl)methyl-1H-imidazol-2-ylmethyl carbonate disclosed in WO 96/10019 and under clinical development by Agouron Pharmaceuticals, Inc., LaJolla Calif. 92037-1020; MKC-442 (1-(ethoxy-methyl)-5-(1-methylethyl)-6-(phenylmethyl)-(2, 4(1H,3H)-pyrimidinedione) discovered by Mitsubishi Chemical Co. and under development by Triangle Pharmaceuticals, Durham, N.C. 27707; and (+)-calanolide A (NSC-675451) and B, coumarin derivatives disclosed in NIH U.S. Pat. No. 5,489,697, licensed to Med Chem Research, which is co-developing (+) calanolide A with Vita-invest as an orally administrable product.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN (available from Merck) as well as nonpeptide protease inhibitors e.g., VIRACEPT (available from Agouron).

Typical suitable PIs include saquinavir (Ro 31-8959) available in hard gel capsules under the INVIRASE tradename and as soft gel capsules under the FORTOVASE tradename from Roche Pharmaceuticals, Nutley, N.J. 07110-1199; ritonavir (ABT-538) available under the NORVIR tradename from Abbott Laboratories, Abbott Park, Ill. 60064; indinavir (MK-639) available under the CRIXIVAN tradename from Merck & Co., Inc., West Point, Pa. 19486-0004; nelfnavir (AG-1343) available under the VIRACEPT tradename from Agouron Pharmaceuticals, Inc., LaJolla Calif. 92037-1020; amprenavir (141W94), tradename AGENERASE, a non-peptide protease inhibitor under development by Vertex Pharmaceuticals, Inc., Cambridge, Mass. 02139-4211 and available from Glaxo-Wellcome, Research Triangle, N.C. under an expanded access program; lasinavir (BMS-234475) available from Bristol-Myers Squibb, Princeton, N.J. 08543 (originally discovered by Novartis, Basel, Switzerland (CGP-61755); DMP-450, a cyclic urea discovered by Dupont and under development by Triangle Pharmaceuticals; BMS-2322623, an azapeptide under development by Bristol-Myers Squibb, Princeton, N.J. 08543, as a 2nd-generation HIV-1 PI; ABT-378 under development by Abbott, Abbott Park, Ill. 60064; and AG-1549 an orally active imidazole carbamate discovered by Shionogi (Shionogi #S-1153) and under development by Agouron Pharmaceuticals, Inc., LaJolla Calif. 92037-1020.

Other antiviral agents include hydroxyurea, ribavirin, IL-2, IL-12, pentafuside and Yissum Project No. 11607. Hydroxyurea (Droxia), a ribonucleoside triphosphate reductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN (aldesleukin) tradename from Chiron Corp., Emeryville, Calif. 94608-2997 as a lyophilized powder for IV infusion or sc administration upon reconstitution and dilution with water; a dose of about 1 to about 20 million IU/day, sc is preferred; a dose of about 15 million IU/day, sc is more preferred. IL-12 is disclosed in WO96/25171 and is available from Roche Pharmaceuticals, Nutley, N.J. 07110-1199 and American Home Products, Madison, N.J. 07940; a dose of about 0.5 microgram/kg/day to about 10 microgram/kg/day, sc is preferred. Pentafuside (DP-178, T-20) a 36-amino acid synthetic peptide, is disclosed in U.S. Pat. No. 5,464,933 licensed from Duke University to Trimeris which is developing pentafuside in collaboration with Duke University; pentafuside acts by inhibiting fusion of HIV-1 to target membranes. Pentafuside (3–100 mg/day) is given as a continuous sc infusion or injection together with efavirenz and 2 PI's to HIV-1 positive patients refractory to a triple combination therapy; use of 100 mg/day is preferred. Yissum Project No.11607, a synthetic protein based on the HIV -1 Vif protein, is under preclinical development by Yissum Research Development Co., Jerusalem 91042, Israel. Ribavirin, 1-β-D-ribofuranosyl-1H-1,2,4-triazole-3-carboxamide, is available from ICN Pharmaceuticals, Inc., Costa Mesa, Calif.; its manufacture and formulation are described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART-multidrug combination therapies include:

(a) triple combination therapies such as two NRTIs and one PI; or (b) two NRTIs and one NNRTI ; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is prefered unless there is intolerance to PIs. Drug compliance is essential. The $CD4^+$ and HIV-1-RNA plasma levels should be monitored every 3–6 months. Should viral load plateau, a fourth drug, e.g., one PI or one NNRTI could be added. See the table below wherein typical therapies are further described:

ANTI-HIV-1 MULTI DRUG COMBINATION THERAPIES

A. Triple Combination Therapies

1. Two NRTIs[1] + one PI[2]
2. Two NRTIs[1] + one NNRTI[3]

B. Quadruple Combination Therapies[4]

Two NRTIs + one PI + a second PI or one NNRTI

ANTI-HIV-1 MULTI DRUG COMBINATION THERAPIES -continued

C. ALTERNATIVES:[5]

Two NRTI[1]
One NRTI[5] + one PI[2]
Two PIs[6] ± one NRTI[7] or NNRTI[3]
One PI[2] + one NRTI[7] + one NNRTI[3]

FOOTNOTES TO TABLE
[1]One of the following: zidovudine + lamivudine; zidovudine + didanosine; stavudine + lamivudine; stavudine + didanosine; zidovudine + zalcitabine
[2]Indinavir, nelfinavir, ritonavir or saquinavir soft gel capsules.
[3]Nevirapine or delavirdine.
[4]See A–M. Vandamne et al Antiviral Chemistry & Chemotherapy 9: 187 at p 193–197 and FIGS. 1 + 2.
[5]Alternative regimens are for patients unable to take a recommended regimen because of compliance problems or toxicity, and for those who fail or relapse on a recommended regimen. Double nucleoside combinations may lead to HIV-resistance and clinical failure in many patients.
[6]Most data obtained with saquinavir and ritonavir (each 400 mg bid).
[7]Zidovudine, stavudine or didanosine.

Agents known in the treatment of rheumatoid arthritis, transplant and graft v. host disease, inflammatory bowel disease and multiple sclerosis which can be administered in combination with the CCR5 antagonists of the present invention are as follows:

solid organ transplant rejection and graft v. host disease: immune suppressants such as cyclosporine and Interleukin-10 (IL-10), tacrolimus, antilymphocyte globulin, OKT-3 antibody, and steroids;

inflammatory bowel disease: IL-10 (see U.S. Pat. No. 5,368,854), steroids and azulfidine;

rheumatoid arthritis: methotrexate, azathioprine, cyclophosphamide, steroids and mycophenolate mofetil;

multiple sclerosis: interferon-beta, interferon-alpha, and steroids.

Certain CCR5 antagonist compounds of the invention may exist in different isomeric (e.g., enantiomers, diastereoisomers and atropisomers) forms. The invention contemplates all such isomers both in pure form and in admixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of the invention can be made by the procedures known in the art, for example by the procedures described in the following reaction schemes, and by the methods described in the examples below.

The following solvents and reagents used in the general reaction schemes and the specific examples may be referred to herein by the abbreviations indicated: tetrahydrofuran (THF); methanol (MeOH); ethyl acetate (EtOAc); trifluoroacetic anhydride (TFAA); dimethylformaldehyde (DMF); benzotriazole (Bt); 1-hydroxy-benzotriazole (HOBT); triethylamine (Et$_3$N); diethyl ether (Et$_2$O); tert-butoxycarbonyl (BOC); N,N,N-diisopropylethylamine (iPr$_2$NEt); and 1-(3-dimethylaminopropyl)-3-ethylcarbodiimide hydrochloride (EDC). Room temperature is rt. Additional abbreviations include: phenyl (Ph); methyl (Me); ethyl (Et); and acetyl (Ac).

Compounds of formula Ia wherein Q is N, Z is CH, X is N, $R^2$ is H, $R^3$ is not H (but is otherwise is as defined above when $R^2$ is H), $R^6$ is methyl, and $R^1$ and $R^8$ are as defined above are prepared according to the following reaction Scheme A ($R^4$ is shown as methyl, and R, $R^5$ and $R^7$ are shown as H, but compounds wherein R, $R^4$, $R^5$ and $R^7$ are other variables can be similarly prepared):

Scheme A

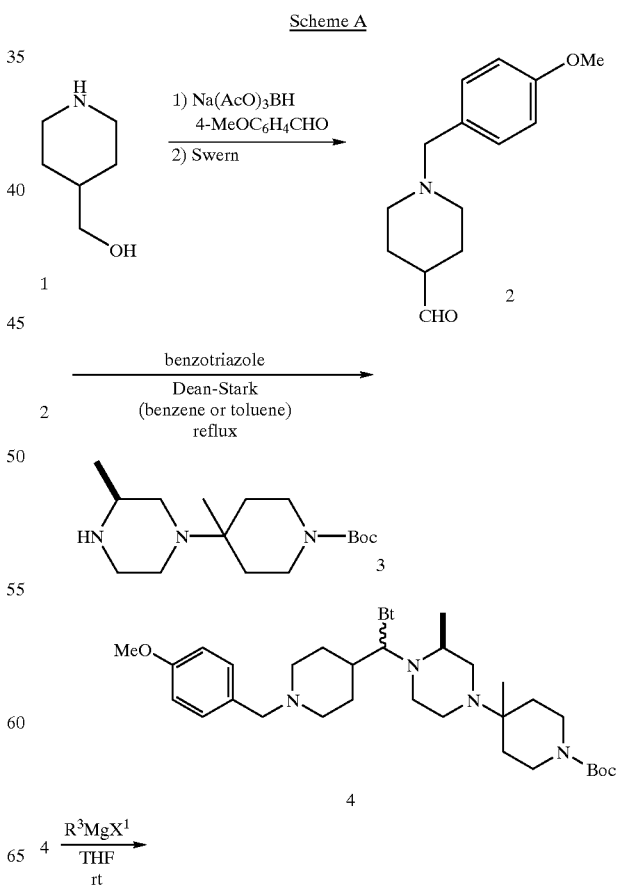

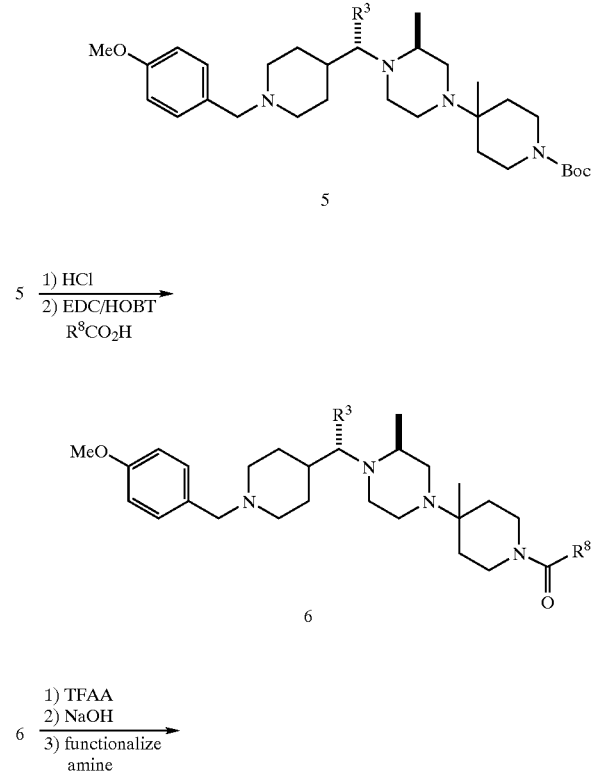

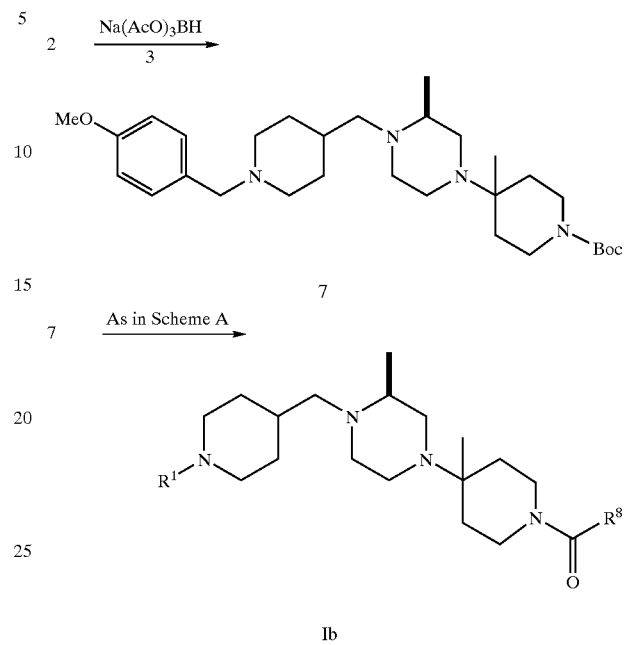

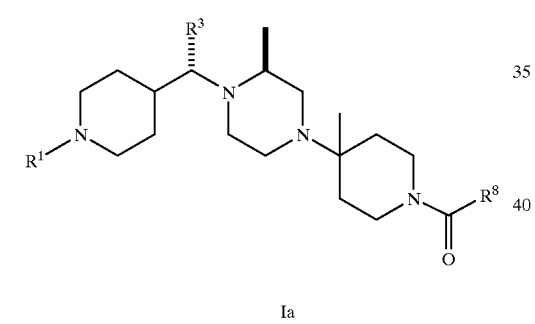

For the synthesis of compounds of formula Ia, the alcohol 1 is protected and oxidized to the aldehyde 2. A solution of aldehyde 2, benzotriazole, and piperidino-piperazine 3 are heated in toluene or benzene with removal of water. The solution is cooled and the solvent removed in vacuo. The adduct 4 is treated with a grignard reagent ($R^3MgX^1$, wherein $R^3$ is as defined above and $X^1$ is, e.g., Br or Cl) which affords a derivative of formula 5. The BOC group in 4 is removed (HCL), and the piperidine NH is coupled to an aryl acid to give amide 6. The 4-methoxy benzyl group in 6 is removed by sequential treatment with TFAA and aqueous 1N NaOH. The piperidine can be functionalized with various reagents, e.g., treatment with $R^1SO_2Cl$ affords a compound of formula Ia wherein $R^1$ is $R^1$—$SO_2$—.

Similar compounds wherein $R^6$ is hydrogen can be prepared by using a des-methyl piperidino-piperazine in place of compound 3.

Compounds of formula Ib wherein Q is N, Z is CH, X is N, $R^2$ and $R^3$ are both H, and $R^1$ and $R^8$ are as defined above are prepared according to the following reaction Scheme B ($R^4$ and $R^6$ are shown as methyl, and $R^5$ and $R^7$ are shown as H, but other definitions of $R^4$–$R^7$ can be similarly prepared):

The aldehyde 2 is reacted with piperidino-piperazine 3 and sodium triacetoxy borohydride to obtain the derivative 7. This compound is processed similarly as above for 5 to obtain compounds of formula Ib.

Compounds of formula Ic wherein Q is N or CH, Z is N, X is CH, $R^2$ and $R^3$ are both H, and R, $R^1$, $R^4$, $R^5$, $R^6$, $R^7$ and $R^8$ are as defined above are prepared according to the following reaction Scheme C:

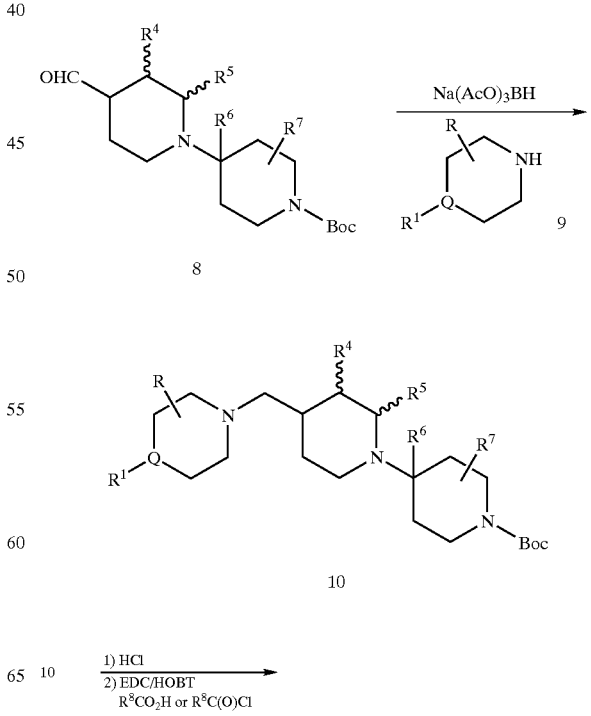

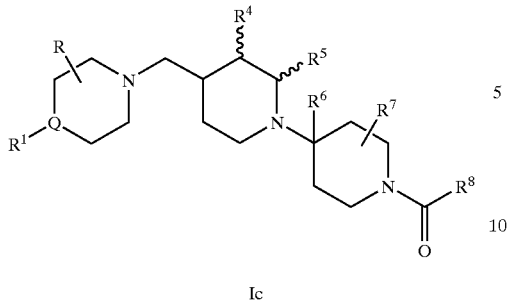

Ic

The aldehyde 8 can be reacted with Na(AcO)$_3$BH and piperazine (Q=N) or piperidine (Q=CH) 9 to obtain compound 10. After removal of the Boc group in 10 and standard amidation (EDC/HOBT/R$^8$CO$_2$H or R$^8$CO$_2$H) of the secondary amine, the amide of type Ic is prepared.

Compounds of formula Id wherein Q and Z are N, X is CH, R$^2$ is H, R$^3$ is not H (but is otherwise is as defined above when R$^2$ is H), and R, R$^1$, R$^4$, R$^5$, R$^6$, R$^7$ and R$^8$ are as defined above are prepared according to the following reaction Scheme D:

Scheme D

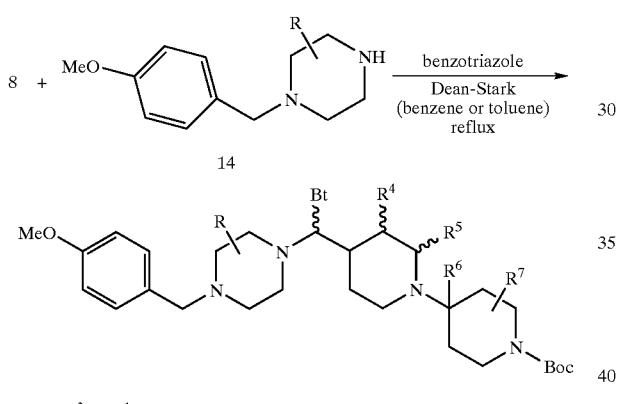

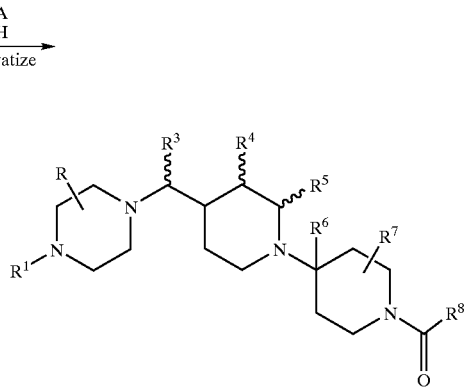

Id

The aldehyde 8 is reacted with piperazine 14 and benzotriazole to form the adduct 15. The benzotriazole group in 15 is displaced by a grignard reagent (R$^3$MgX$^1$) or organo-zinc reagent (R$^3$ZnX$^1$) to obtain 16. Removal of the BOC group in 16, followed by standard coupling conditions know to those skilled in the art, gives the amide 17. The 4-methoxy benzyl group in 17 is removed and the resultant secondary amine is functionalized according to standard conditions to obtain compounds with the general structure Id.

Piperidinyl compounds of formula Ie similar to piperazinyl compounds of formula Id are prepared according to Scheme E:

Scheme E

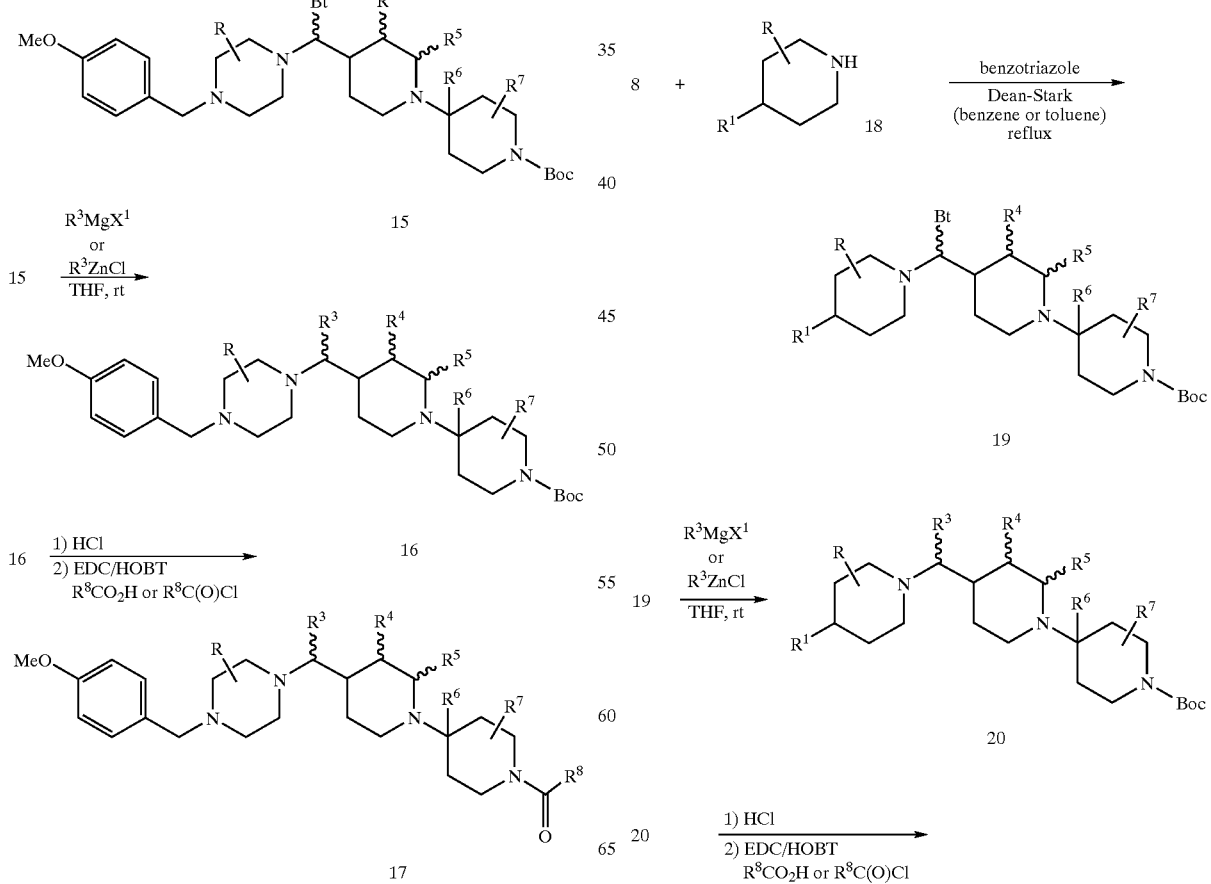

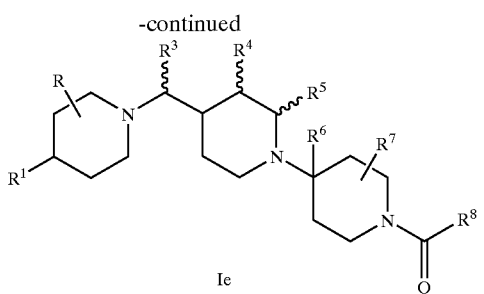

Ie

The aldehyde 8, piperidine 18, and benzotriazole are condensed to form the adduct 19. The benzotriazole (Bt) group is displaced in 19 to give the compound 20. Deprotection and standard amidation give the compound Ie.

Compounds of formula If wherein Q is N, Z and X are CH, $R^2$ is H, $R^3$ is optionally substituted phenoxy or pyridyloxy, and R, $R^1$, $R^4$, $R^5$, $R^6$, $R^7$ and $R^8$ are as defined above are prepared according to the following reaction Scheme F:

Scheme F

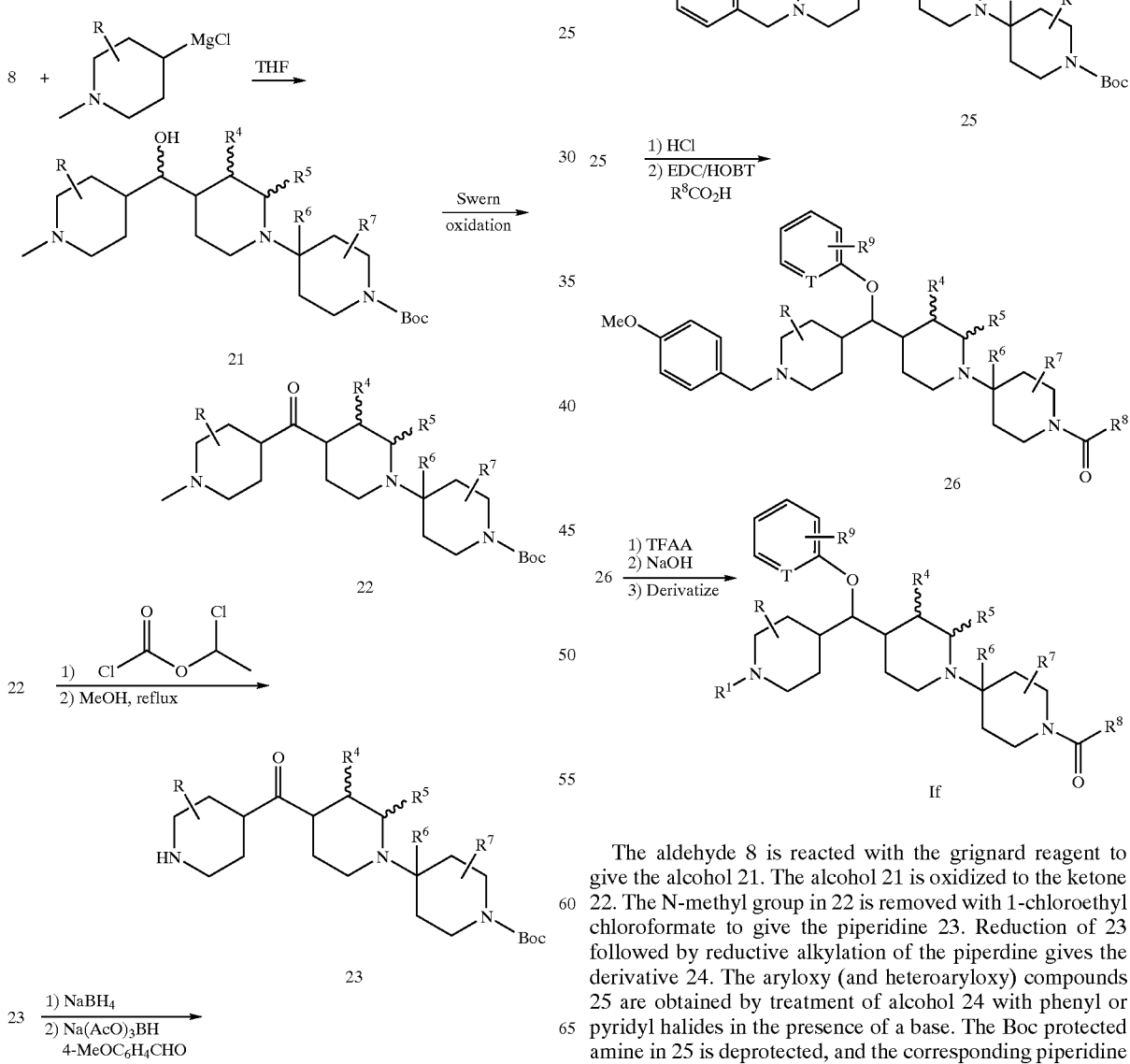

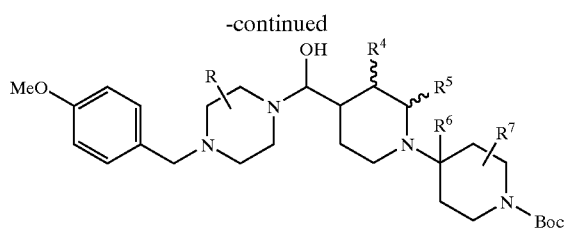

The aldehyde 8 is reacted with the grignard reagent to give the alcohol 21. The alcohol 21 is oxidized to the ketone 22. The N-methyl group in 22 is removed with 1-chloroethyl chloroformate to give the piperidine 23. Reduction of 23 followed by reductive alkylation of the piperdine gives the derivative 24. The aryloxy (and heteroaryloxy) compounds 25 are obtained by treatment of alcohol 24 with phenyl or pyridyl halides in the presence of a base. The Boc protected amine in 25 is deprotected, and the corresponding piperidine is subjected to standard amidation conditions ($R^8$COOH, EDCI or DEC, and HOBT, or $R^8C(O)Cl$). The 4-methoxy benzyl group in 26 is removed, and the free piperidinyl NH is derivatized with alkyl halides, acyl chorides, alkyl chloroformates, isocyanides, alkyl sulfonyl halides, aryl sulfonyl halides, and reductive alkylation methods (Na(AcO)$_3$BH/aldehyde or ketone) to obtain compounds of formula If.

Compounds of formula Ig wherein Q is N, Z and X are CH, $R^2$ is H, $R^3$ is alkyl-C(O)O—, alkyl-NH—C(O)O— or —OC(O)—N(alkyl)$_2$, and R, $R^1$, $R^4$, $R^5$, $R^6$, $R^7$ and $R^8$ are as defined above are prepared according to the following reaction Scheme G:

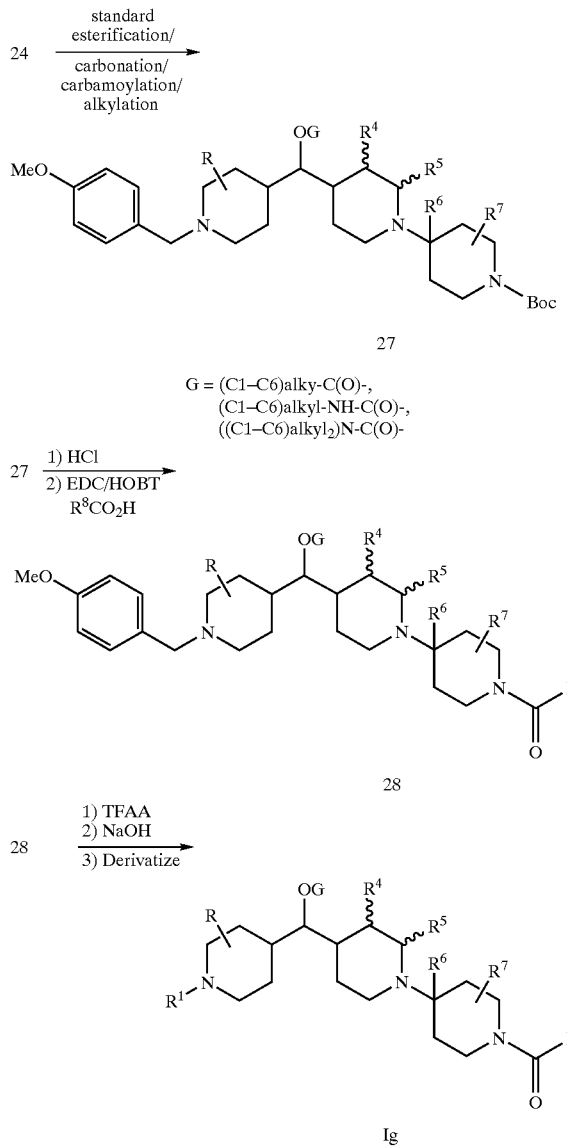

The hydroxyl group in 24 is derivatized using alkyl halides, acyl chlorides, alkyl chloroformates, and isocyanides to give compounds 28. Deprotection/amidation of 27 gives the amide 28. Deprotection of the benzyl group in 28 and derivatization of the piperidine give the compounds of formula Ig.

Compounds of formula Ih wherein Q is N, Z and X are CH, $R^2$ is H, $R^3$ is alkyl-C(O)—NH—, alkyl-NH—C(O)NH— or and R, $R^1$, $R^4$, $R^5$, $R^6$, $R^7$ and $R^8$ are as defined above are prepared according to the following reaction Scheme H:

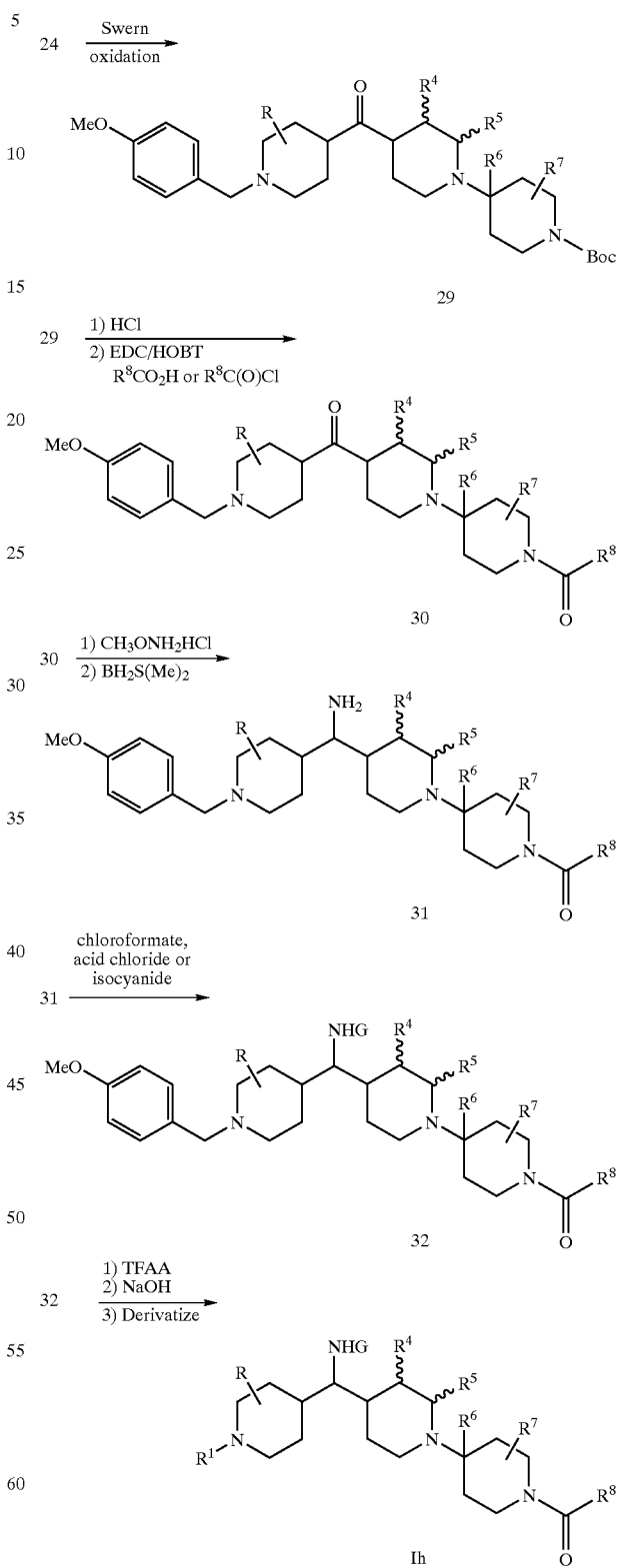

The alcohol 24 is oxidized (DMSO/oxalyl chloride, Swern conditions) to the ketone 29. Deprotection/standard amidation of 29 gives the amide 30. The ketone 30 is condensed with $CH_3ONH_2$ HCl to give an oxime. The oxime is reduced with $BH_3$ $S(CH_3)_2$ to obtain the amine 31. The amine 31 is reacted with chloroformates, acid chlorides, or isocyanides to furnish carbamates, esters, and ureas, respectively, of formula 32 wherein G is as defined above. Deprotection of the benzyl group in 32 and derivatization of the piperidine give the compounds of formula Ih.

Oximes of formula Ii wherein Q is N, Z and X are CH, $R^2$ and $R^3$ together are =$NOR^{10}$, and $R^{10}$, R, $R^1$, $R^4$, $R^5$, $R^6$, $R^7$ and $R^8$ are as defined above are prepared according to the following reaction Scheme I:

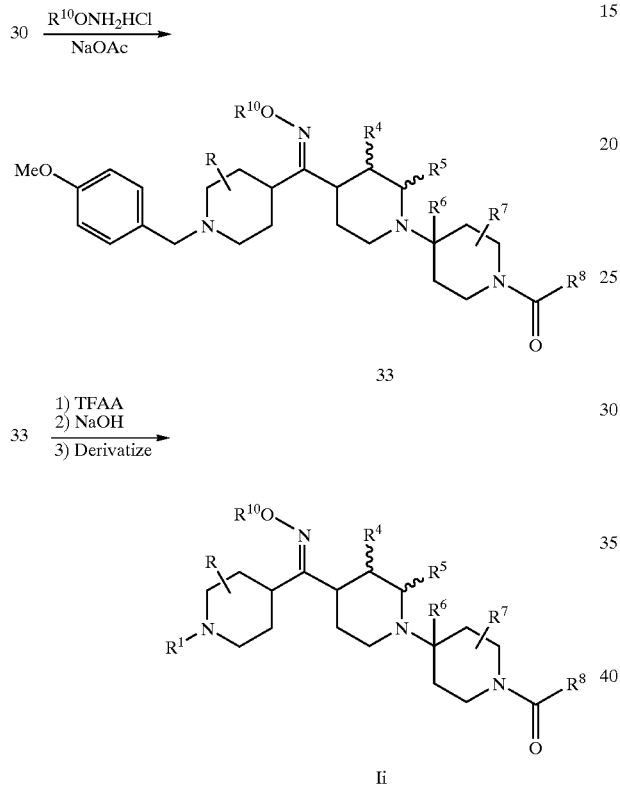

The ketone 30 is condensed with subsituted hydroxylamines to obtain the oximes 33. The 4-methoxy group in 33 is removed and functionalized as previously described to obtain the compounds of formula Ii.

Compounds of formula Ij wherein Q, Z and X are each N, $R^2$ and $R^3$ together are =O, and R, $R^1$, $R^4$, $R^5$, $R^6$, $R^7$ and $R^8$ are as defined above are prepared according to the following reaction Scheme J:

Scheme J

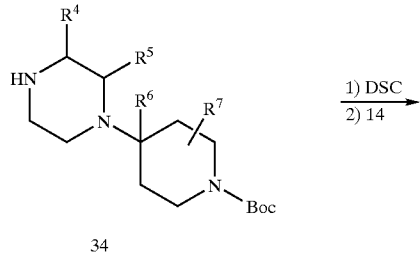

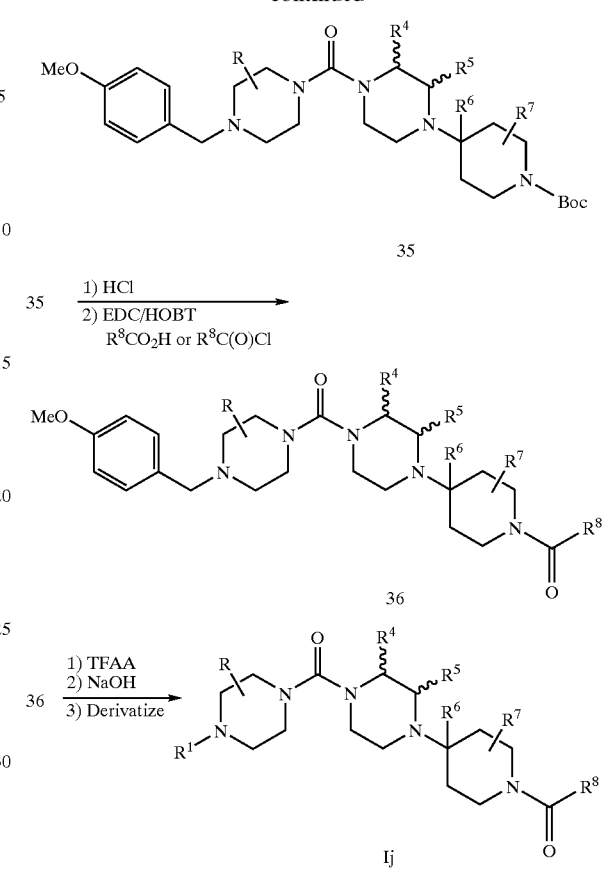

The piperidino-piperazine 34 is sequentially reacted with N,N'-disuccinimidyl carbonate (DSC) and piperazine 14 to obtain the urea 35. The Boc derivative 35 is processed to 36 and Ij using conditions described in Scheme A.

Compounds of formula Ik wherein Q is N or CH, Z and X are each N, $R^2$ and $R^3$ together are =NH, and R, $R^1$, $R^4$, $R^5$, $R^6$, $R^7$ and $R^8$ are as defined above are prepared by several methods, for example according to the following reaction Scheme K:

Scheme K

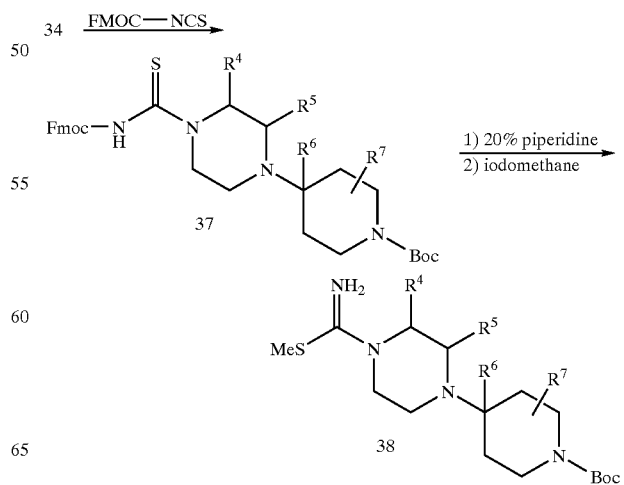

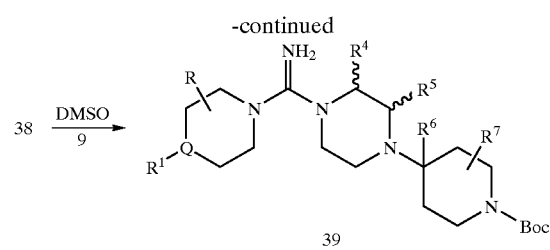

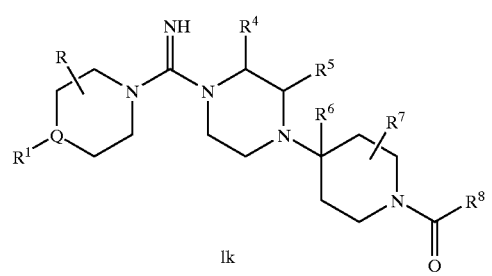

The piperidino-piperazine 34 can be converted into the guanidine 39 by the method shown above. The guanidine 39 can be converted into the amides of formula Ik by the methods described in Scheme A.

Compounds useful in this invention are exemplified by the following preparative examples, which should not be construed to limit the scope of the disclosure. Alternative mechanistic pathways and analogous structures within the scope of the invention may be apparent to those skilled in the art.

EXAMPLE 1

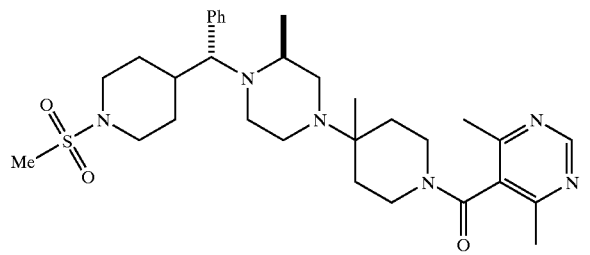

Step 1

The alcohol 1 (2.0 g, 17 mmol), 4-methoxy benzaldehyde (2.5 ml, 21 mmol), and Na(AcO)$_3$BH (4.4 g, 21 mmol) were taken up in CH$_2$Cl$_2$ (50 ml) and stirred at 25° C. for 22 h. The solution was diluted with CH$_2$Cl$_2$ and washed with aqueous 1N NaOH. The aqueous layer was extracted with CH$_2$Cl$_2$. The combined organic layers were dried (Na$_2$SO$_4$), filtered and concentrated. The residue was partitioned between Et$_2$O and 1 M HCl. The acidic, aqueous layer was extracted with Et$_2$O. The aqueous layer was cooled to 0° C. Solid NaOH pellets were added until the pH=11–12. The basic, aqueous layer was extracted with CH$_2$Cl$_2$. The CH$_2$Cl$_2$ layers were dried (Na$_2$SO$_4$), filtered, and concentrated to obtain the benzyl protected piperdino-alcohol (2.92 g, 73%).

DMSO (1.3 ml, 19 mmol) was taken up in CH$_2$Cl$_2$ (80 ml), and the resulting solution was cooled to −40° C. (CO$_2$/CH$_3$CN). Oxalyl chloride (1.6 ml, 19 mmol) was added slowly to the solution at −40° C. The solution was allowed to stir at 40° C. for 0.5 h. The N-(4-methoxybenzyl)-piperdino-alcohol (2.92 g, 12 mmol) was added as a solution in CH$_2$Cl$_2$ (15 ml) to the reaction mixture at −40° C. The resulting solution was stirred at −40° C. for 0.5 h. Et$_3$N (5.2 ml, 37 mmol) was added to the solution at −40° C. The resulting white slurry was stirred tor 20 min. at that temperature. The mixture was diluted with CH$_2$Cl$_2$ and washed with aqueous 1 N NaOH. The aqueous layer was extracted with CH$_2$Cl$_2$. The combined CH$_2$Cl$_2$ layers were dried (Na$_2$SO$_4$), filtered, and concentrated to obtain the aldehyde 2 as a yellow oil (2.8 g, 97%).

Step 2

The aldehyde 2 (392 mg, 1.68 mmol), piperidino-piperazine 3 (500 mg, 1.68 mmol), and benzotriazole (200 mg, 1.68 mmol) were taken up in toluene (20 ml) and heated at reflux with removal of water (Dean-Stark trap). After 2 h, the solution was cooled and concentrated to obtain 1.0 g (100%) of the benzotriazole adduct 4 as a light brown gum.

Step 3

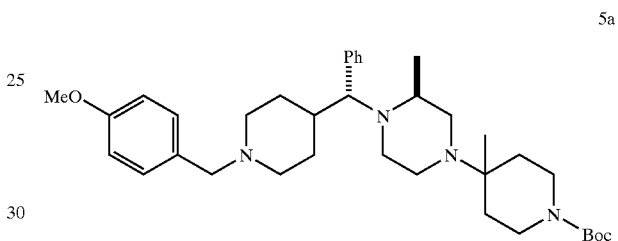

The product of Step 2 (300 mg, 0.48 mmol) was taken up in THF (4 ml) under an atmosphere of N$_2$. A solution of PhMgBr (0.4 ml, 3.0 M in Et$_2$O) was added to the solution at 25° C. The solution was stirred at that temperature for 2 h. The reaction mixture was partitioned between EtOAc and sat. NH$_2$Cl. The aqeuous layer was extracted with EtOAc. The combined EtOAc layers were washed with brine and dried (Na$_2$SO$_4$). Filtration and concentration furnished a yellow oil. The material was purified by preparative thin-layer chromatography (2/1 hexanes/acetone, SiO$_2$) to obtain 207 mg (73%) of compound 5a as a yellow oil.

Step 4

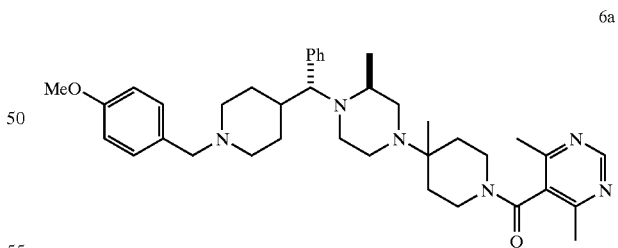

Compound 5a (200 mg, 0.34 mmol) and 4.0 M HCl in dioxane (1 ml) were taken up in MeOH (5 ml) and stirred at 25° C. for 2 h. The solution was concentrated to give 189 mg (93%) of the deprotected piperidine as the tri-hydrochloride salt.

The salt (189 mg, 0.32 mmol), EDC (92 mg, 0.48 mmol), HOBT (65 mg, 0.48 mmol), 4,6-dimethyl-3-pyrimidine carboxylic acid (73 mg. 0.48 mmol), iPr$_2$NEt (0.4 ml, 2.24 mmol) were taken up in DMF (5 ml) and stirred at 25° C. for 17 h. The solution was partitioned between EtOAc and 1 N NaOH. The aqueous layer was extracted with EtOAc. The combined EtOAc layers were washed with brine and dried (Na$_2$SO$_4$). Filtration and concentration gave the crude product. Purification by preparative thin-layer chromatography (95/5 EtOAc/Et$_3$N, SiO$_2$) gave 144 mg (72%) of amide 6a as a colorless oil. HRMS (MH$^+$) found: 625.4222.

Step 5

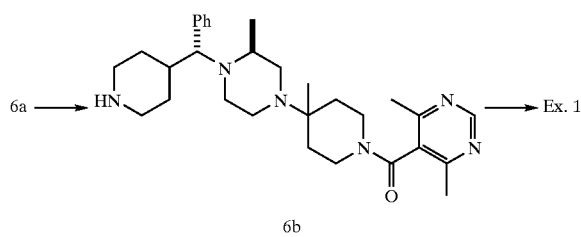

6a → 6b → Ex. 1

Compound 6a (129 mg, 0.21 mmol) and iPr$_2$NEt (0.11 ml, 0.63 mmol) were taken up in CH$_2$Cl$_2$ (6 ml). TFAA (0.080 ml, 0.31 mmol) was added to the solution. The solution was stirred at 25° C. for 0.5 h, then concentrated. The residue was taken up in MeOH, and 1 N NaOH was added to the solution. The solution was stirred at 25° C. for 2.5 h, then concentrated. The residue was partitioned between CH$_2$Cl$_2$ and 1 N NaOH. The aqueous layer was extracted with CH$_2$Cl$_2$. The combined organic layers were dried (Na$_2$SO$_4$), filtered, and concentrated to obtain a mixture of example 6b and 4-methoxy benzyl alcohol. Example 6b was purified by crystallization of the corresponding HCl salt. HRMS (MH$^+$) found:505.3661.

The free base of example 6b (42 mg, 0.08 mmol) and MeSO$_2$Cl (0.020 ml) were partitioned between CH$_2$Cl$_2$ and 1 N NaOH. The solution was stirred at 25° C. for 4 h. The layers were separated, and the aqueous layer was extracted with CH$_2$Cl$_2$. The combined organic layers were dried (Na$_2$SO$_4$), filtered, and concentrated. The residue was purified by thin layer chromatography (95/5 EtOAc/Et$_3$N, SiO$_2$) to give the title compound as a colorless oil. The bis-HCl salt was formed by dissolving the free-base in EtOAc followed by trituration with 2 M HCl in Et$_2$O, HRMS (MH$^+$) found:583.3425.

Using a similar procedure and the appropriate reagents, compounds of the structure

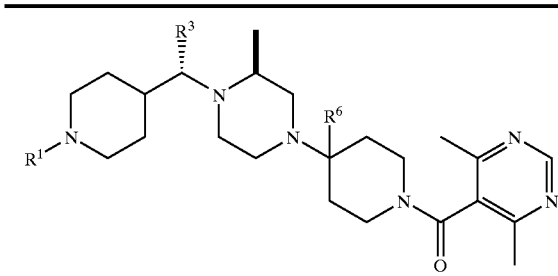

were prepared, wherein R$^1$, R$^3$ and R$^6$ are as defined in the following table:

| Ex. | R$^1$ | R$^3$ | R$^6$ | HRMS (MH$^+$) found |
|---|---|---|---|---|
| 1A | 4-CH$_3$OC$_6$H$_4$CH$_2$ | 4-CF$_3$C$_6$H$_5$ | CH$_3$ | 693.4112 |
| 1B | H | 4-CF$_3$C$_6$H$_5$ | CH$_3$ | 573.3637 |
| 1C | CH$_3$SO$_2$ | 4-CF$_3$C$_6$H$_5$ | CH$_3$ | 651.3311 |
| 1D | 4-CH$_3$OC$_6$H$_4$CH$_2$ | CH$_2$CH$_2$CH$_3$ | CH$_3$ | 591.4386 |
| 1E | 4-CH$_3$OC$_6$H$_4$CH$_2$ | CH(CH$_3$)$_2$ | CH$_3$ | 591.4392 |

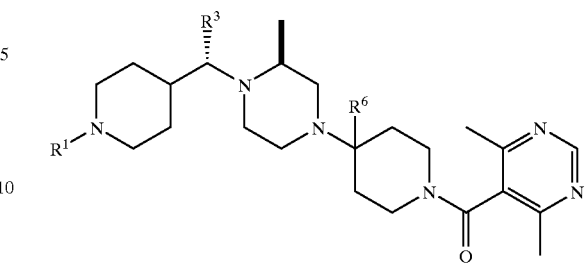

were prepared, wherein R$^1$, R$^3$ and R$^6$ are as defined in the following table:

| Ex. | R$^1$ | R$^3$ | R$^6$ | HRMS (MH$^+$) found |
|---|---|---|---|---|
| 1F | 4-CH$_3$OC$_6$H$_4$CH$_2$ | CH$_2$C$_6$H$_5$ | CH$_3$ | 639.4399 |
| 1G | 4-CH$_3$OC$_6$H$_4$CH$_2$ | CH$_3$ | CH$_3$ | 563.4079 |
| 1H | 4-CH$_3$OC$_6$H$_4$CH$_2$ | CH$_2$CH$_3$ | CH$_3$ | 577.4226 |
| 1I | H | CH$_2$CH$_2$CH$_3$ | CH$_3$ | 471.3802 |
| 1J | CH$_3$SO$_2$ | CH$_2$CH$_2$CH$_3$ | CH$_3$ | 549.3580 |
| 1K | 4-CH$_3$OC$_6$H$_4$CH$_2$ | cyclopentyl | CH$_3$ | 617.4543 |
| 1L | H | CH(CH$_3$)$_2$ | CH$_3$ | 471.3815 |
| 1M | CH$_3$SO$_2$ | CH(CH$_3$)$_2$ | CH$_3$ | 549.3580 |
| 1N | 4-CH$_3$C$_6$H$_4$SO$_2$ | CH(CH$_3$)$_2$ | CH$_3$ | 625.3917 |
| 1O | 4-CH$_3$C$_6$H$_4$SO$_2$ | CH$_2$CH$_2$CH$_3$ | CH$_3$ | 625.3895 |
| 1P | CH$_3$SO$_2$ | cyclopentyl | CH$_3$ | 575.3746 |
| 1Q | 4-CH$_3$C$_6$H$_4$SO$_2$ | cyclopentyl | CH$_3$ | 651.4055 |
| 1R | H | cyclopentyl | CH$_3$ | 497.3966 |
| 1S | 4-CH$_3$C$_6$H$_4$SO$_2$ | C$_6$H$_5$ | CH$_3$ | 659.3752 |
| 1T | EtNHC(O) | C$_6$H$_5$ | CH$_3$ | 576.4028 |
| 1U | C$_6$H$_5$NHC(O) | C$_6$H$_5$ | CH$_3$ | 624.4027 |
| 1V | H | cyclohexyl | CH$_3$ | 511.4120 |
| 1W | 4-CH$_3$OC$_6$H$_4$CH$_2$ | CH$_2$CH$_2$CH$_3$ | H | 577.4230 |
| 1X | 4-CH$_3$OC$_6$H$_4$CH$_2$ | CH$_2$C$_6$H$_5$ | H | 625.4221 |
| 1Y | 4-CH$_3$OC$_6$H$_4$CH$_2$ | C$_6$H$_5$ | H | 611.4089 |
| 1Z | 4-CH$_3$OC$_6$H$_4$SO$_2$ | C$_6$H$_5$ | CH$_3$ | 675.3684 |
| 1AA | 3-Cl—C$_6$H$_4$SO$_2$ | C$_6$H$_5$ | CH$_3$ | 679.3188 |
| 1AB | CH$_3$SO$_2$ | CH$_2$C$_6$H$_5$ | CH$_3$ | 597.3583 |
| 1AC | CH$_3$ | C$_6$H$_5$ | CH$_3$ | 519.3815 |
| 1AD | 3-Cl—C$_6$H$_4$SO$_2$ | CH$_2$C$_6$H$_5$ | CH$_3$ | 693.3345 |
| 1AE | CH$_3$CH$_2$SO$_2$ | CH$_2$C$_6$H$_5$ | CH$_3$ | 611.3737 |
| 1AF | 4-CH$_3$OC$_6$H$_4$SO$_2$ | 4-F—C$_6$H$_4$ | CH$_3$ | 693.3609 |
| 1AG | CH$_3$SO$_2$ | 4-F—C$_6$H$_4$ | CH$_3$ | 601.3326 |
| 1AH | 3-Cl—C$_6$H$_4$SO$_2$ | 4-F—C$_6$H$_4$ | CH$_3$ | 697.3112 |
| 1AI | 4-CH$_3$OC$_6$H$_4$CH$_2$ | 3-F—C$_6$H$_4$ | CH$_3$ | 643.4142 |
| 1AJ | CF$_3$C(O) | 4-F—C$_6$H$_4$CH$_2$ | CH$_3$ | 633.3552 |
| 1AK | CH$_3$SO$_2$ | 3-F—C$_6$H$_4$ | CH$_3$ | 601.3326 |
| 1AL | 3-Cl—C$_6$H$_4$SO$_2$ | 3-F—C$_6$H$_4$ | CH$_3$ | 697.3105 |
| 1AM | 4-CH$_3$OC$_6$H$_4$SO$_2$ | 3-F—C$_6$H$_4$ | CH$_3$ | 693.3609 |
| 1AN | CH$_3$SO$_2$ | 4-F—C$_6$H$_4$CH$_2$ | CH$_3$ | 615.3482 |
| 1AO | 3-Cl—C$_6$H$_4$SO$_2$ | 4-F—C$_6$H$_4$CH$_2$ | CH$_3$ | 711.3250 |
| 1AP | 4-CH$_3$OC$_6$H$_4$SO$_2$ | 4-F—C$_6$H$_4$CH$_2$ | CH$_3$ | 707.3751 |
| 1AQ | 4-CH$_3$OC$_6$H$_4$CH$_2$ | 2-thienyl | CH$_3$ | 631.3805 |
| 1AR | CF$_3$CH$_2$SO$_2$ | C$_6$H$_5$ | CH$_3$ | 651.3201 |
| 1AS | CF$_3$SO$_2$ | C$_6$H$_5$ | CH$_3$ | 637.3156 |
| 1AT | 4-CH$_3$OC$_6$H$_4$CH$_2$ | 3-thienyl | CH$_3$ | 631.3784 |
| 1AU | 3-Cl—C$_6$H$_4$SO$_2$ | 2-thienyl | CH$_3$ | 685.2768 |
| 1AV | 4-CH$_3$OC$_6$H$_4$SO$_2$ | 2-thienyl | CH$_3$ | 681.3266 |
| 1AW | CH$_3$SO$_2$ | 2-thienyl | CH$_3$ | 589.3002 |
| 1AX | CH$_3$SO$_2$ | 3-thienyl | CH$_3$ | 589.3002 |
| 1AY | 3-Cl—C$_6$H$_4$SO$_2$ | 3-thienyl | CH$_3$ | 685.2750 |
| 1AZ | 4-F—C$_6$H$_4$SO$_2$ | CH$_2$C$_6$H$_5$ | CH$_3$ | 677.3633 |
| 1BA | 2-thienyl-SO$_2$ | CH$_2$C$_6$H$_5$ | CH$_3$ | 665.3317 |
| 1BB | C$_6$H$_5$SO$_2$ | CH$_2$C$_6$H$_5$ | CH$_3$ | 653.3748 |
| 1BC | CF$_3$SO$_2$ | CH$_2$C$_6$H$_5$ | CH$_3$ | 651.3317 |
| 1BD | CF$_3$CH$_2$SO$_2$ | CH$_2$C$_6$H$_5$ | CH$_3$ | 665.3449 |
| 1BE | (CH$_3$)$_2$NSO$_2$ | CH$_2$C$_6$H$_5$ | CH$_3$ | 626.3859 |
| 1BF | cyclopropyl-SO$_2$ | 3-F—C$_6$H$_4$ | CH$_3$ | 627.3503 |
| 1BG | 4-F—C$_6$H$_4$SO$_2$ | 3-F—C$_6$H$_4$ | CH$_3$ | 681.3406 |
| 1BH | 4-CH$_3$OC$_6$H$_4$CH$_2$ | n-Butyl | CH$_3$ | 605.4556 |
| 1BI | 3-Cl—C$_6$H$_4$SO$_2$ | n-Butyl | CH$_3$ | 659.3501 |

-continued

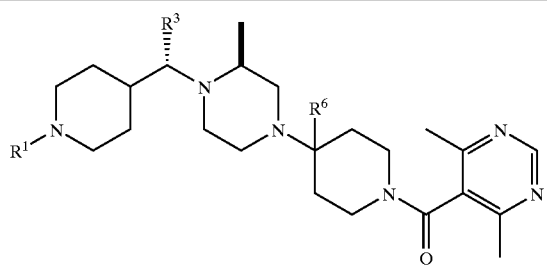

were prepared, wherein $R^1$, $R^3$ and $R^6$ are as defined in the following table:

| Ex. | $R^1$ | $R^3$ | $R^6$ | HRMS (MH$^+$) found |
|---|---|---|---|---|
| 1BJ | 4-CH$_3$OC$_6$H$_4$SO$_2$ | n-Butyl | CH$_3$ | 655.4009 |
| 1BK | 3-Cl—C$_6$H$_4$SO$_2$ | 3-pyridyl | CH$_3$ | 680.3166 |
| 1BL | 4-CH$_3$OC$_6$H$_4$SO$_2$ | 3-pyridyl | CH$_3$ | 676.3637 |
| 1BM | 3-Cl—C$_6$H$_4$SO$_2$ | 2-pyridyl | CH$_3$ | 680.3160 |
| 1BN | cyclopropyl-SO$_2$ | C$_6$H$_5$ | CH$_3$ | 609.3598 |
| 1BO | 4-CH$_3$OC$_6$H$_4$CH$_2$ | 2-pyrimidyl | CH$_3$ | 627.4128 |
| 1BP | CH$_3$CH$_2$SO$_2$ | C$_6$H$_5$ | CH$_3$ | 597.3598 |
| 1BQ | CH$_3$CH$_2$CH$_2$SO$_2$ | C$_6$H$_5$ | CH$_3$ | 611.3749 |
| 1BR | i-propyl-SO$_2$ | C$_6$H$_5$ | CH$_3$ | 611.3749 |
| 1BS | CH$_3$C(O) | C$_6$H$_5$ | CH$_3$ | 547.3768 |
| 1BT | CH$_3$SO$_2$ | 2-pyrimidyl | CH$_3$ | 585.3343 |
| 1BU | cyclopropyl-C(O) | C$_6$H$_5$ | CH$_3$ | 573.3923 |
| 1BV | CH$_3$CH$_2$C(O) | C$_6$H$_5$ | CH$_3$ | 561.3928 |
| 1BW | i-propyl-C(O) | C$_6$H$_5$ | CH$_3$ | 575.4075 |
| 1BX | 3-Cl—C$_6$H$_4$SO$_2$ | 4-pyridyl | CH$_3$ | 680.3133 |
| 1BY | 4-CH$_3$OC$_6$H$_4$CH$_2$ | 3,5-difluorophenyl | CH$_3$ | 661.4035 |
| 1BZ | cyclopropyl-SO$_2$ | 3,5-difluorophenyl | CH$_3$ | 645.3388 |
| 1CA | CH$_3$SO$_2$ | cyclohexyl | CH$_3$ | 589.3904 |

Details of the preparation of 1BF

Step A

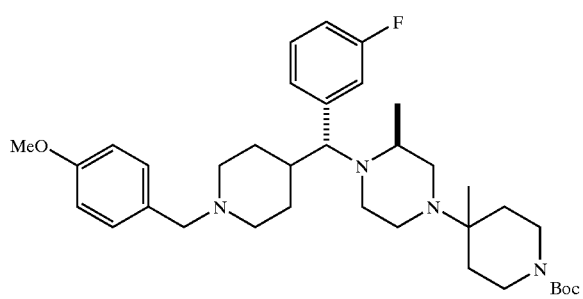

The product of Example 1, Step 2 (1.0 g, 1.6 mmol) was taken up in THF (10 ml) under an atmosphere of N$_2$ and a solution of 3-fluorophenylmagnesium bromide (13 ml, 0.5 M in Et$_2$O) was added at 25° C. The solution was stirred at 25° C. for 6 h. The reaction mixture was poured into a separatory funnel containing 25% aqueous sodium citrate. The aqeuous layer was extracted with EtOAc, the combined EtOAc layers were washed with brine and dried (Na$_2$SO$_4$). Filtration and concentration furnished a yellow oil. The material was purified by flash chromatography (3/1 hexanes/acetone, SiO$_2$) which gave 640 mg (66%) of compound 5b as a yellow oil.

Step B

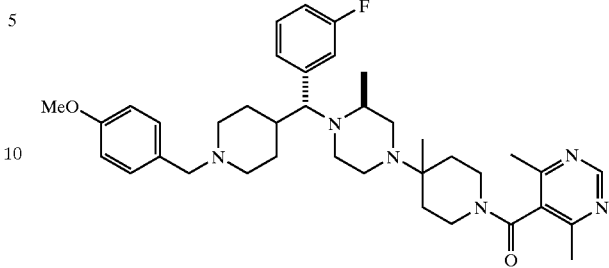

5b (640 mg, 1.05 mmol) was deprotected according to the procedure of Example 1, Step 4 to obtain the deprotected piperidine. The piperidine (533 mg, 0.32 mmol), EDC (400 mg, 0.48 mmol), HOBT (280 mg, 0.48 mmol), 4,6-dimethyl-3-pyrimidine-5-carboxylic acid (240 mg. 0.48 mmol) and iPr$_2$NEt (0.72 ml, 2.24 mmol) were taken up in DMF (5 ml) and subjected to conditions described above in Step 4 to furnish 414 mg (62%) of 6b as a yellow oil.

Step C

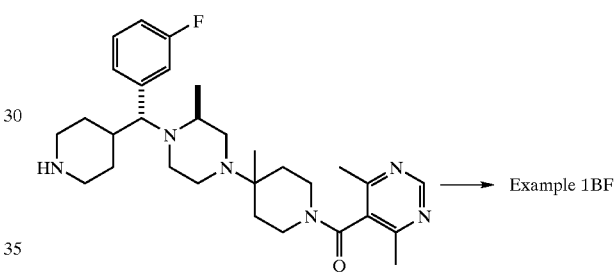

→ Example 1BF 6c (400 mg, 0.62 mmol) was treated according to the procedure of Example 1, Step 5, to obtain 6d. The free base 6d (0.07 g, 0.13 mmol), cyclopropylsulfonyl chloride (0.02 g, 0.14 mmol) and Et$_3$N (0.091 ml) were taken up in CH$_2$Cl$_2$ and the solution was stirred at rt for 4 h. The solution was concentrated on the rotovap. The residue was purified via preparative thin-layer chromatography (10/1 EtOAc/EtOH, SiO$_2$) to obtain 14 mg (17%) of 1BF as a colorless oil. The bis-HCl salt was formed as described above for 6a. M.p.= 206–210° C.

EXAMPLE 2

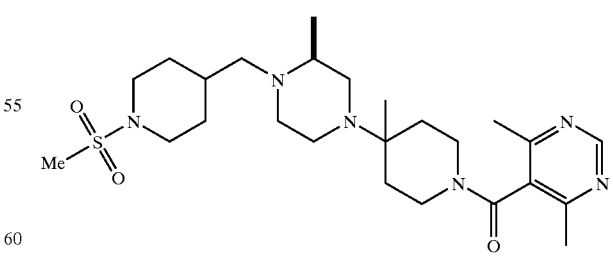

The aldehyde 2 (0.93 g, 4.0 mmol), piperidino-piperazine 3 (1.0 g, 3.4 mmol), and Na(AcO)$_3$BH (860 mg, 4.0 mmol) were taken up in CH$_2$Cl$_2$. (10 ml) and stirred at 25° C. for 18 h. The solution was diluted with CH$_2$Cl$_2$ and washed with 1N NaOH. The aqueous layer was extracted with CH$_2$Cl$_2$.

The combined organic layers were dried (Na$_2$SO$_4$), filtered, and concentrated. Purifification via flash chromatography (acetone/CH$_2$Cl$_2$ gradient 2/5–3/5, SiO$_2$) gave 1.24 g (71%) of 7 as a colorless oil.

Compound 7 was treated according to the procedures in Steps 4 and 5 of Example 1 to obtain the title compound. HRMS (MH$^+$) found: 507.3122.

Using a similar procedure and the appropriate reagents, compounds of the structure

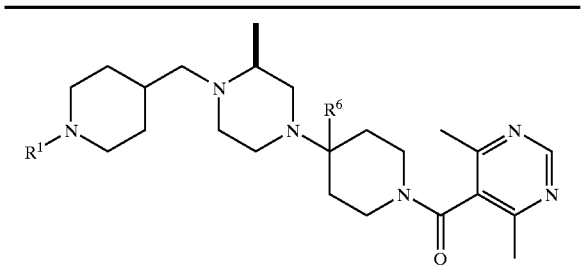

were prepared, wherein R$^1$ and R$^6$ are as defined in the following table:

| Ex. | R$^1$ | R$^6$ | HRMS (MH$^+$) found |
|-----|-------|-------|---------------------|
| 2A | H | CH$_3$ | 429.3340 |
| 2B | 4-CH$_3$OC$_6$H$_4$CH$_2$ | CH$_3$ | 548.3838 |
| 2C | CF$_3$SO$_2$ | CH$_3$ | 561.2840 |
| 2D | C$_6$H$_5$C(O) | CH$_3$ | 533.3611 |
| 2E | 4-CH$_3$C$_6$H$_4$SO$_2$ | CH$_3$ | 583.3442 |

EXAMPLE 3

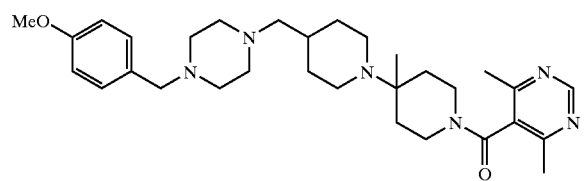

Step 1

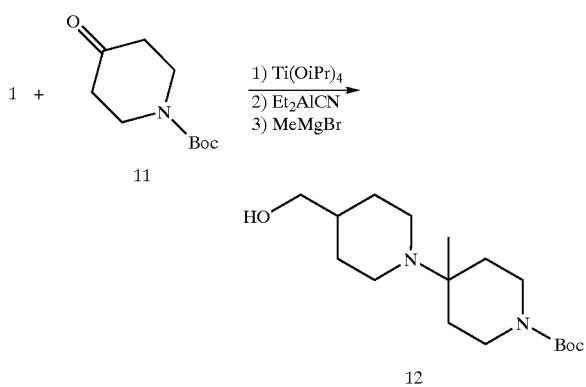

The alcohol 1 (2.0 g, 17.4 mmol), N-Boc-4-piperidone 11 (3.5 g, 17.4 mmol) and Ti(OiPr)$_4$ (5.7 ml, 19 mmol) were taken up in CH$_2$Cl$_2$ (60 ml) and stirred at 25° C. for 64 h. Diethyl aluminum cyanide (42 ml of a 1.0 M solution in toluene, 42 mmol) was added to the reaction mixture at 25° C. The solution was stirred at 25° C. for an additional 24 h. The solution was poured in a flask containing EtOAc and sat. aqueous NaHCO$_3$ at 0° C. The mixture was filtered through a plug of Celite. The layers were separated, and the aqueous layer was extracted with EtOAc. The combined organic layers were washed with brine and dried (Na$_2$SO$_4$). Filtration and concentration gave the crude cyanide (4.87 g, 87%) as a yellow oil.

The cyanide (4.87 g, 15 mmol) was taken up in THF (75 ml). CH$_3$MgBr (25 ml of a 3.0 M solution in Et$_2$O) was added to the reaction mixture at 0° C. The solution was allowed to warm to 25° C. and was stirred at that temperature for 18 h. The solution was partitioned between 25 wt % aqueous solution of sodium citrate and EtOAc. The aqueous layer was extracted with EtOAc. The combined EtOAc layers were washed with brine and dried (Na$_2$SO$_4$). Filtration and concentration gave a yellow oil. Purification via flash chromatography (95/5 to 90/10 EtOAc/MeOH. SiO$_2$) gave 3.7 g (79%) of the piperidino-piperidine 12 as a yellow gum.

Step 2

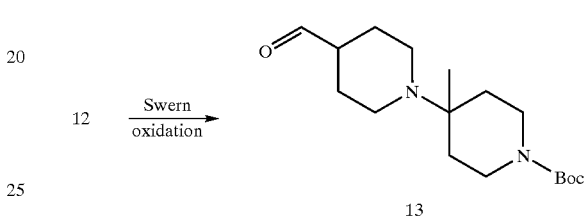

DMSO (1.26 ml, 17.8 mmol) was taken up in CH$_2$Cl$_2$ (140 ml). The solution was cooled to −40° C. (CH$_3$CN/CO$_2$). Oxalyl chloride (1.6 ml, 17.8 mmol) was added dropwise to the solution at −40° C. The solution was stirred at that temperature for 0.75 h. The alcohol 12 (3.7 g, 11.9 mmol) in CH$_2$Cl$_2$ was added to the reaction mixture at −40° C. The resulting solution was stirred at that temperature for 0.75 h. Et$_3$N (5.0 ml, 35.7 mmol) was added to the reaction mixture at −40° C. The white slurry was stirred at −40° C. for 0.5 h. The mixture was diluted with CH$_2$Cl$_2$ and washed with 1 N NaOH. The aqueous layer was extracted with CH$_2$Cl$_2$. The combined organic layers were dried (Na$_2$SO$_4$), filtered, and concentrated to obtain 3.5 g (95%) of aldehyde 13 as a yellow oil.

Step 3

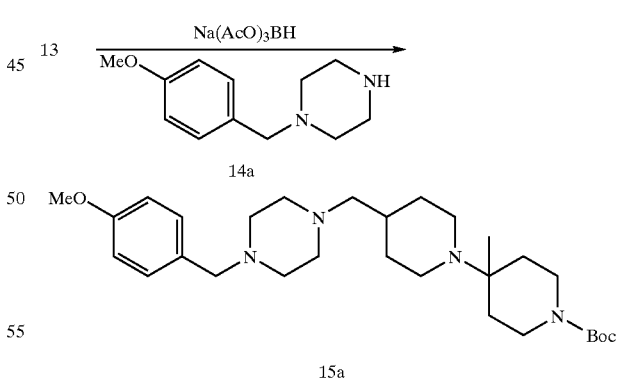

The piperazine 14a (133 mg, 0.65 mmol), aldehyde 13 (200 mg, 0.65 mmol), and Na(AcO)$_3$BH (165 mg, 0.78 mmol) were taken up in CH$_2$Cl$_2$ and stirred at 25° C. for 20 h. The solution was diluted with CH$_2$Cl$_2$ and washed with 1 N NaOH. The aqueous layer was extracted with CH$_2$Cl$_2$. The combined CH$_2$Cl$_2$ layers were dried (Na$_2$SO$_4$), filtered, and concentrated. Purification via preparative thin-layer chromatography (1/1 hexanes/acetone, SiO$_2$) gave 160 mg (46%) of 15a as an oil.

Step 4

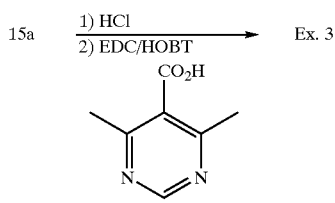

The Boc group in 15a was removed, and the resulting piperidine was coupled to the pyrimidine acid as described in Scheme A, Step 4, to obtain the title compound as an oil: HRMS (MH$^+$) found: 535.3765.

Other R$^1$ derivatives can be prepared via deprotection of the 4-methoxy benzyl group and subsequent derivatization as described previously in Scheme A.

EXAMPLE 4

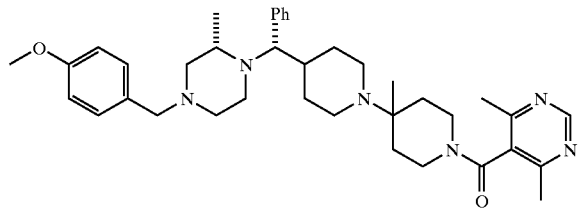

Steps 1–2

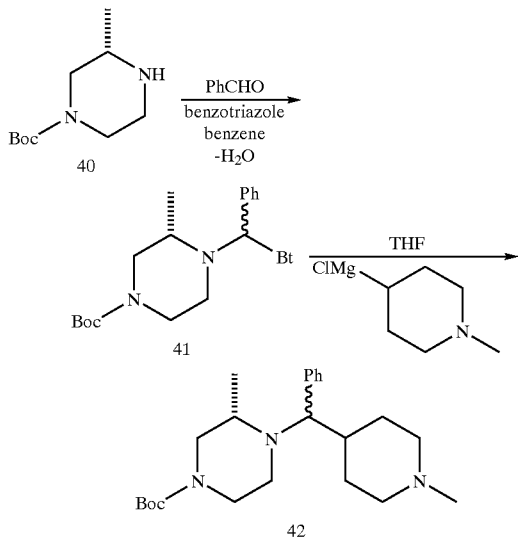

Step 1

N-Boc-(S)-methyl piperazine 40 (4.35 g, 21.8mmol), benzaldehyde (2.2 ml, 22 mmol), and benzotriazole (2.59 g, 21.8 mmol) were taken up in benzene and heated to reflux with removal of water (Dean-Stark trap). After heating at 110° C. for 4 h, the solution was cooled and concentrated to furnish 8.9 g (Quant.) of the benzotriazole adduct 41 as a foam.

Step 2

41 (1.4 g, 3.4 mmol) was taken up in THF (25 ml). A THF solution of the piperidinyl grignard (13.7 ml of a 1.0 M solution) was added to 41 at 25° C. The solution was stirred at that temperature for 5 h. The reaction mixture was poured into a separatory funnel containing EtOAc and 25 wt % sodium citrate. The aqueous solution was extracted with EtOAc. The combined EtOAc layers were washed with brine and dried (Na$_2$SO$_4$). Filtration and concentration gave a yellow oil. Purification via flash chromatography (15/1 CH$_2$Cl$_2$/7N NH$_3$ in CH$_3$OH, SiO$_2$) gave 954 mg (72%) of the piperazine-piperidine 42 as a mixture of isomers.

Steps 3–4

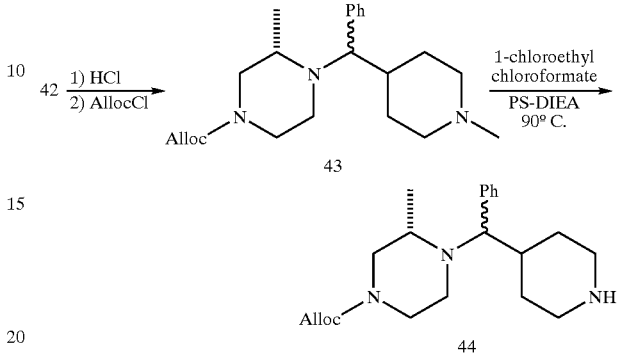

Step 3

42 (954 mg, 2.46 mmol) was taken up in CH$_3$OH (15 ml), and 3 ml of a 4.0 M HCl solution in dioxane was added. The solution was stirred at 25° C. for 18 h, then concentrated to give deprotected piperazine as the HCl salt. The crude salt (2.46 mmol) was partitioned between EtOAc and water. K$_2$CO$_3$ (2.0 grams, 14.8 mmol) and allyl chloroformate (0.34 ml, 3.2 mmol) were added to the mixture. The mixture was stirred vigorously at 25° C. for 20 h. The aqueous layer was extracted with EtOAc, the combined EtOAc layers were washed with brine and dried (Na$_2$SO$_4$). Filtration and concentration gave the allyloxycarbonyl (Alloc) protected piperazine 43 as a mixture of isomers.

Step 4

43 was taken up in 1,2-dichloroethane. 1-Chloro-ethyl chloroformate (0.5 ml, 4.9 mmol) and polystyrene bound Hunig's base (PS-DIEA; DIEA is diisopropyl-ethylamide) (2.7 g) were heated at 90° C. for 1.5 h. The solution was cooled and concentrated. The residue was taken up in CH$_3$OH and refluxed for 1 h. The solution was concentrated, and the residue was partitioned between CH$_2$Cl$_2$ and 1 N NaOH$_{(aq)}$. The aqueous layer was extracted with CH$_2$Cl$_2$. The combined organic layers were dried (Na$_2$SO$_4$), filtred and concentrated to give 752 mg (85%) of 44 as a mixture of isomers.

Steps 5–6

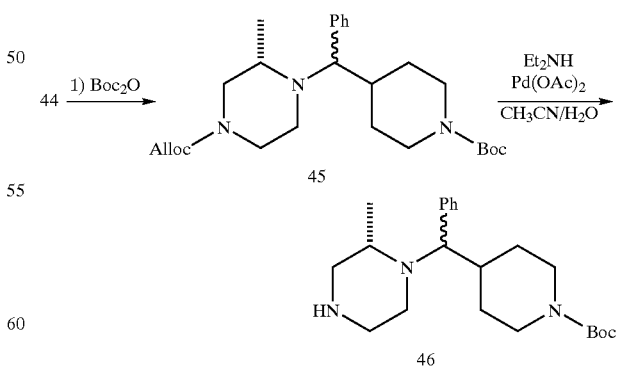

Step 5

44 (752 mg, 2.10 mmol), di-t-butyl-dicarbonate (550 mg, 2.5 mmol), and K$_2$CO$_3$ (870 mg, 6.3 mmol) were partitioned between EtOAc and H$_2$O. The aqueous layer was extracted with EtOAc. the combined EtOAc layers were washed with brine and dried with $Na_2SO_4$. Filtration and concentration gave the crude N-Boc piperidine 45 as a yellow oil. Purification via flash chromatography (4/1 hexanes/EtOAc, $SiO_2$) gave 606 mg (63%) of 45 as a colorless foam.

Step 6

45 (606 mg, 1.3 mmol), $Et_2NH$ (2.7 ml, 26.5 mmol), and 3,3',3"-phosphinidyne-tris(benzenesulfonic acid), trisodium salt (30 mg, 0.052 mmol) were taken up in $CH_3CN/H_2O$ (1/1 40 ml). $Pd(OAc)_2$ (6 mg, 0.026 mmol) was added and the solution was stirred at 25° C. for 3 h. The solution was concentrated, and the residue was partitioned between EtOAc and 1 N $NaOH_{(aq.)}$. The aqueous layer was extracted with EtOAc, the combined organic layers were washed with brine and dried ($Na_2SO_4$). Filtration and concentration gave 500 mg (99%) of 46 as a mixture of isomers.

Steps 7–8

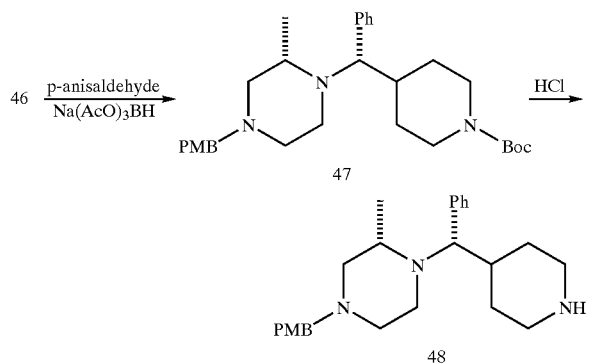

Step 7

46 (500 mg, 1.3 mmol), p-anisaldehyde (1.2 ml, 1.6 mmol), and $Na(AcO)_3BH$ (340 mg, 1.6 mmol) were taken up in $CH_2Cl_2$ and stirred at 25° C. (18 h). The solution was diluted with $CH_2Cl_2$ and washed with 1 N $NaOH_{(aq.)}$. The aqueous layer was extracted with $CH_2Cl_2$, the combined organic layers were dried ($Na_2SO_4$), filtered and concentrated to give the crude p-methoxybenzyl (PMB) protected piperazine 47 as a mixture of isomers. Purification via flash chromatography (6/1 hexanes/EtOAc, $SiO_2$) gave 713 mg of 47 as a semisolid (mixture of isomers). Purification via recrystallization (hexanes/$CH_2Cl_2$) gave 220 mg (34%) of the (S,S) isomer 47 as white needles.

Step 8

47 (220 mg, 0.45 mmol) and 4.0 M HCl in dioxane (2 ml) were taken up in $CH_3OH$ and stirred at 25° C. (4 h). The solution was concentrated, and the residue was partitioned between $CH_2Cl_2$ and 1 N $NaOH_{(aq.)}$. The aqueous layer was extracted with $CH_2Cl_2$. The combined organic layers were dried ($Na_2SO_4$). Filtration and concentration gave 182 mg (100%) of 48 as a colorless oil.

Steps 9–10

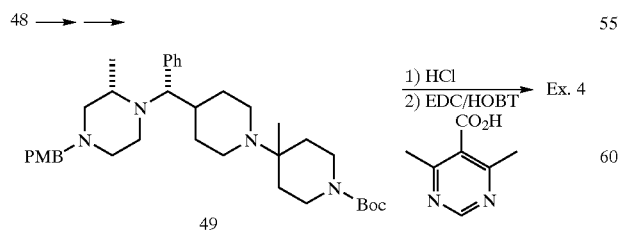

Step 9

48 was derivatized into 49 using the procedure of Example 3, Step 1.

Step 10

The Boc group in 49 was removed (HCl), and the resulting piperidine was coupled to the pyrimidine acid as described in Scheme A to furnish the title compound as a yellow oil: $HRMS(MH^+)$ found: 625.4235.

Using similar procedures and the appropriate reagents, compounds of the structure

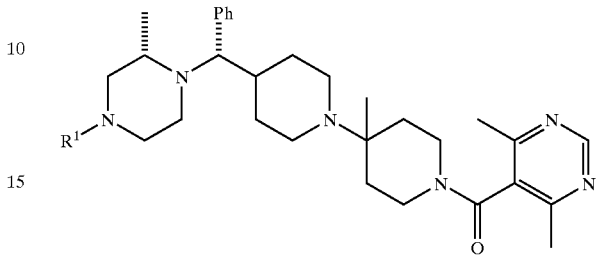

were prepared, where $R^1$ is defined in the following table:

| Ex. | $R^1$ | HRMS ($MH^+$) found |
|---|---|---|
| 4A | $CH_3SO_2$ | 583.3419 |
| 4B | 3-Cl—$C_6H_4SO_2$ | 679.3204 |

EXAMPLE 5

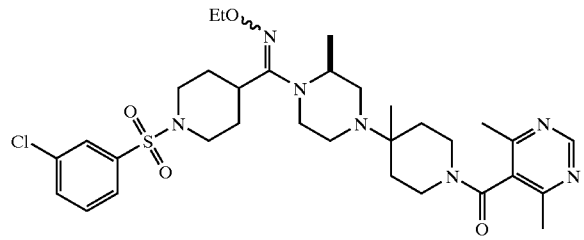

Step 1

1) AllocCl
2) TFA
3) EDC/HOBT

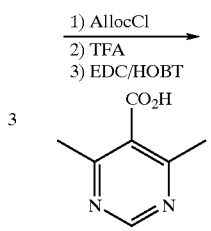

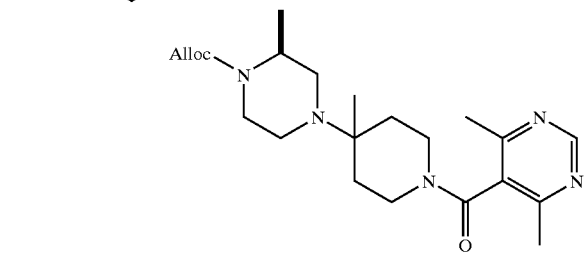

Compound 3 (2 g, 6.7 mmol), allyl chloroformate (0.93 ml, 8.7 mmol), and $K_2CO_3$ (5.6 g, 40 mmol) were partitioned between EtOAc and $H_2O$. The mixture was stirred vigorously at 25° C. (24 h). The layers were separated, and the aqueous layer was extracted with EtOAc. The combined EtOAc layers were washed with brine and dried (Na₂SO₄). Filtration and concentration gave 2.6 g (100%) of the alloc protected piperazine as a thick yellow oil.

The Boc group was removed, and the resulting piperidine was coupled to the pyrimidine acid as described in Scheme A, Step 4, to obtain 2.3 g (85% from 3) to the piperidine-amide 50 as a yellow foam.

Steps 2–3

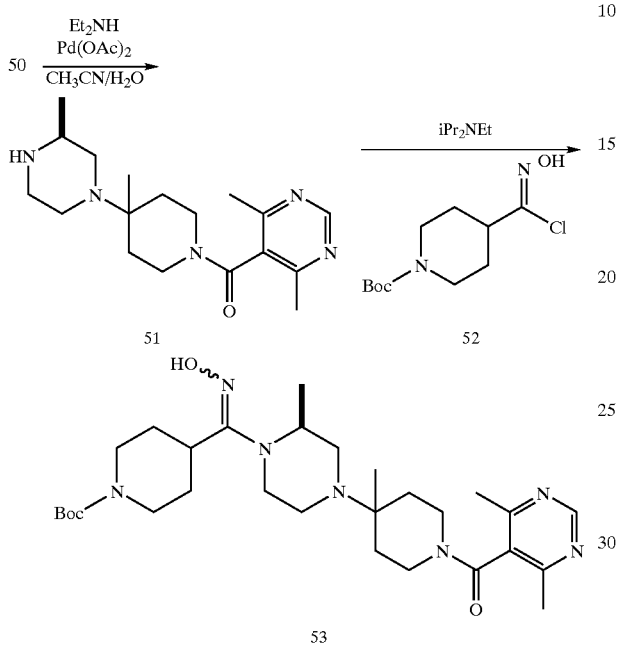

The Alloc group in 50 was removed according to the conditions described for the conversion of 45 to 46 above in Example 4 which furnished piperazine 51.

51 (450 mg, 1.36 mmol), imidoyl chloride 52 (360 mg, 1.36 mmol), and iPr₂NEt (1.2 ml, 6.8 mmol) were taken up in CH₂Cl₂ and stirred at 25° C. (18 h). The solution was diluted with CH₂Cl₂ and washed with water. The aqueous layer was extracted with CH₂Cl₂. The combined organic layers were dried (Na₂SO₄). Filtration and concentration gave the crude amide-oxime 53. Purification via preparative thin-layer chromatography (95/5 EtOAc/Et₃N, SiO₂) gave 550 mg (72%) of amide-oxime 53 as a mixture of isomers.

Step 4

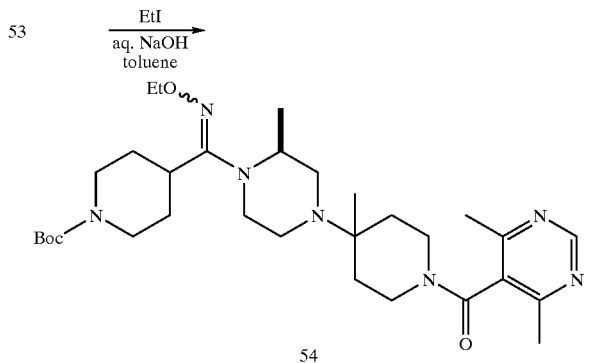

53 (550 mg, 0.99 mmol), EtI (0.16 ml, 1.98 mmol), and Bu₄NHSO₄ (3 mg, 0.01 mmol) were partitioned between toluene and aqueous 50% NaOH. The mixture was stirred vigorously at 25° C. (18 h). The mixture was diluted with EtOAc and water. The aqueous layer was extracted with EtOAc. The combined organic layers were washed with brine and dried (Na₂SO₄). Filtration and concentration gave a yellow oil. Purification via preparative thin-layer chromatography (95/5 EtOAc/Et₃N, SiO2) gave 457 mg (79%) of 54 as a yellow oil (mixture of isomers).

Step 5

The Boc group in 54 was removed by HCl as described in Scheme A, Step 4. The resulting piperidine was reacted with 3-chlorobenzene sulfonyl chloride, according to the procedure described in Example 1, Step 5, second paragraph, to obtain Example 5 as a yellow oil. HRMS(MH⁺): 660.3089.

Using similar procedures and the appropriate reagents, compounds of the structure

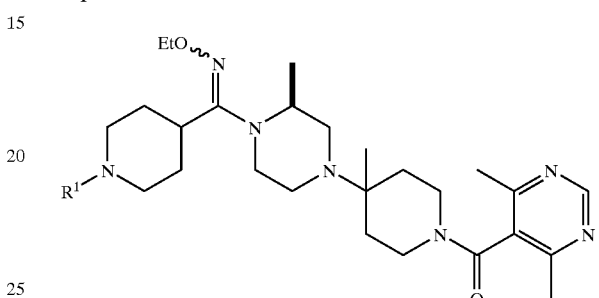

were prepared, where $R^1$ is defined in the following table:

| Ex. | $R^1$ | HRMS (MH⁺) found |
|---|---|---|
| 5A | 4-CH₃OC₆H₄SO₂ | 656.3588 |
| 5B | CH₃SO₂ | 564.3328 |

The following assays can be used to determine the CCR5 inhibitory and antagonistic activity of the compounds of the invention.

CCR5 Membrane Binding Assay

A high throughput screen utilizing a CCR5 membrane binding assay identifies inhibitors of RANTES binding. This assay utilizes membranes prepared from NIH 3T3 cells expressing the human CCR5 chemokine receptor which have the ability to bind to RANTES, a natural ligand for the receptor. Using a 96-well plate format, membrane preparations are incubated with ¹²⁵I-RANTES in the presence or absence of compound for one hour. Compounds are serially diluted over a wide range of 0.001 ug/ml to 1 ug/ml and tested in triplicates. Reaction cocktails are harvested through glass fiber filters, and washed thoroughly. Total counts for replicates are averaged and data reported as the concentration required to inhibit 50 percent of total ¹²⁵I-RANTES binding. Compounds with potent activity in the membrane binding assay are further characterized in seconday cell-based HIV-1 entry and replication assays.

HIV-1 Entry Assay

Replication defective HIV-1 reporter virions are generated by cotransfection of a plasmid encoding the NL4-3 strain of HIV-1 (which has been modified by mutation of the envelope gene and introduction of a luciferase reporter plasmid) along with a plasmid encoding one of several HIV-1 envelope genes as described by Connor et al, *Virology*, 206 (1995), p. 935–944. Following transfection of the two plasmids by calcium phosphate precipitation, the viral supernatants are harvested on day 3 and a functional viral titer determined. These stocks are then used to infect U87 cells stably expressing CD4 and the chemokine receptor CCR5 which have been preincubated with or without test compound. Infections are carried out for 2 hours at 37° C., the cells washed and media replaced with fresh media containing compound. The cells are incubated for 3 days, lysed and luciferase activity determined. Results are reported as the concentration of compound required to inhibit 50% of the luciferase activity in the control cultures.

HIV-1 Replication Assay

This assay uses primary peripheral blood mononuclear cells or the stable U87-CCR5 cell line to determine the effect of anti-CCR5 compounds to block infection of primary HIV-1 strains. The primary lymphocytes are purified from normal healthy donors and stimulated in vitro with PHA and IL-2 three days prior to infection. Using a 96-well plate format, cells are pretreated with drug for 1 hour at 37° C. and subsequently infected with an M-tropic HIV-1 isolates. Following infection, the cells are washed to remove residual inoculum and cultured in the presence of compound for 4 days. Culture supernatants are harvested and viral replication measured by determination of viral p24 antigen concentration.

Calcium Flux Assay

Cells expressing the HIV coreceptor CCR5 are loaded with calcium sensitive dyes prior to addition of compound or the natural CCR5 ligand. Compounds with agonist properties will induce a calcium flux signal in the cell, while CCR5 antagonists are identified as compounds which do not induce signaling by themselves but are capable of blocking signaling by the natural ligand RANTES.

GTPγS Binding Assay (Secondary Membrane Binding Assay)

A GTPγS binding assay measures receptor activation by CCR5 ligands. This assay measures the binding of $^{35}S$ labeled-GTP to receptor coupled G-proteins that occurs as a result of receptor activation by an appropriate ligand. In this assay, the CCR5 ligand, RANTES, is incubated with membranes from CCR5 expressing cells and binding to the receptor activation (or binding) is determined by assaying for bound $^{35}S$ label. The assay quantitatively determines if compounds exhibit agonist characteristics by inducing activation of the receptor or alternatively antagonist properties by measuring inhibition of RANTES binding in a competitive or non-competitive fashion.

Chemotaxis Assay

The chemotaxis assay is a functional assay which characterizes the agonist vs. antagonist properties of the test compounds. The assay measures the ability of a non-adherent murine cell line expressing human CCR5 (BaF-550) to migrate across a membrane in response to either test compounds or natural ligands (i.e., RANTES, MIP-1β). Cells migrate across the permeable membrane towards compounds with agonist activity. Compounds that are antagonists not only fail to induce chemotaxis, but are also capable of inhibiting cell migration in response to known CCR5 ligands.

The role of CC chemokine receptors such as CCR-5 receptors in inflammatory conditions has been reported in such publications as *Immunology Letters*, 57, (1997), 117–120 (arthritis); *Clinical & Experimental Rheumatology*, 17 (4) (1999), p. 419–425 (rheumatoid arthritis); *Clinical & Experimental Immunology*, 117 (2) (1999), p.237–243 (atopic dermatitis); *International Journal of Immunopharmacology*, 20 (11) (1998), p. 661–7 (psoriasis); *Journal of Allergy & Clinical Immunology*, 100 (6, Pt 2) (1997), p. S52–5 (asthma); and *Journal of Immunology*, 159 (6) (1997), p. 2962–72 (allergies).

In the assay to determine HIV replication, compounds of the invention range in activity from an $IC_{50}$ of about 0.1 to about 1000 nM, with preferred compounds having a range of activity from about 0.1 to about 100 nM, more preferably about 0.1 to about 10 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 10 mg to about 500 mg, preferably from about 25 mg to about 300 mg, more preferably from about 50 mg to about 250 mg, and most preferably from about 55 mg to about 200 mg, according to the particular application.

The actual dosage of the compound of formula I employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 100 mg/day to about 300 mg/day, preferably 150 mg/day to 250 mg/day, more preferably about 200 mg/day, in two to four divided doses.

The doses and dosage regimens of the NRTIs, NNRTIs, PIs and other agents used in combination with the CCR5 antagonist compound will be determined by the attending clinician inview of the approved doses and dosage regimens in the package inserts or as set forth in the protocols, taking into consideration the age, sex and condition of the patient and the severity of the condition treated.

The goal of the HIV-1 therapy of the present invention is to reduce the HIV-1-RNA viral load below the detectable limit. The "detectable limit of HIV-1-RNA" in the context of the present invention means that there are fewer than about 200 to fewer than about 50 copies of HIV-1-RNA per ml of plasma of the patient as measured by quantitative, multi-cycle reverse transcriptase PCR methodology. HIV-1-RNA is preferably measured in the present invention by the methodology of Amplicor -1 Monitor 1.5 (available from Roche Diagnostics) or of Nuclisens HIV-1 QT-1.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the structural formula I

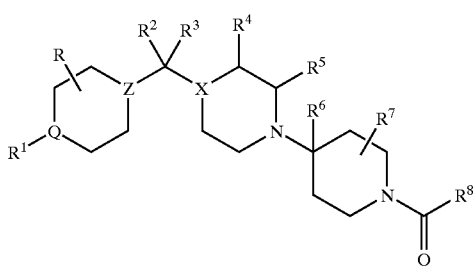

I or a diastereomer, enantiomer, atropisomer or pharmaceutically acceptable salt thereof, wherein:

X is N;

Q and Z are independently selected from the group consisting of CH and N, provided that one or both of Q and Z is N;

R, $R^5$, $R^6$ and $R^7$ are independently selected from the group consisting of H and $(C_1-C_6)$alkyl;

$R^4$ is $(C_1-C_6)$alkyl;

$R^1$ is H, $(C_1-C_6)$alkyl, fluoro-$(C_1-C_6)$alkyl-, $R^9$-aryl $(C_1-C_6)$alkyl-, $R^9$-heteroaryl-$(C_1-C_6)$alkyl-, $(C_1-C_6)$alkyl-$SO_2$—, $(C_3-C_6)$cycloalkyl-$SO_2$—, fluoro-$(C_1-C_6)$alkyl-$SO_2$—, $R^9$-aryl-$SO_2$—, $R^9$-heteroaryl-$SO_2$—, $N(R^{22})(R^{23})$—$SO_2$—, $(C_1-C_6)$alkyl-C(O)—, $(C_3-C_6)$cyclo-alkyl-C(O)—, fluoro-$(C_1-C_6)$alkyl-C(O)—, $R^9$-aryl-C(O)—, NH—$(C_1-C_6)$alkyl-C(O)— or $R^9$-aryl-NH—C(O)—;

$R^2$ is H or $(C_1-C_6)$alkyl, and $R^3$ is H, $(C_1-C_6)$alkyl, $(C_1-C_6)$alkoxyl$(C_1-C_6)$alkyl-, $(C_3-C_{10})$-cycloalkyl-, $(C_3-C_{10})$cycloalkyl$(C_1-C_6)$alkyl-, $R^9$-aryl, $R^9$-aryl $(C_1-C_6)$-alkyl-, $R^9$- heteroaryl, or $R^9$-heteroaryl $(C_1-C_6)$alkyl-, provided that both X and Z are not each N;

or $R^2$ and $R^3$ together are =O, =NOR$^{10}$, or =N—NR$^{11}$R$^{12}$;

$R^8$ is $(R^{14}, R^{15}, R^{16})$-substituted phenyl, $(R^{14}, R^{15}, R^{16})$-substituted pyridyl, $(R^{14}, R^{15}, R^{16})$-substituted pyridyl N-oxide, or $(R^{14}, R^{15}, R^{16})$-substituted pyrimidyl, $R^9$ is 1, 2 or 3 substituents independently selected from the group consisting of H, halogen, $(C_1-C_6)$alkyl, $(C_1-C_6)$alkoxy, —$CF_3$, —$OCF_3$, $CH_3C(O)$—, —CN, $CH_3SO_2$—, $CF_3SO_2$— and —$N(R^{22})(R^{23})$;

$R^{10}$ is H, $(C_1-C_6)$alkyl, fluoro$(C_1-C_6)$alkyl-, $(C_3-C_{10})$ cycloalkyl$(C_1-C_6)$alkyl-, hydroxy$(C_2-C_6)$alkyl-, $(C_1-C_6)$alkyl-O—$(C_2-C_6)$alkyl-, $(C_1-C_6)$alkyl-O—C (O)—$(C_1-C_6)$alkyl- or $N(R^{22})(R^{23})$—C(O)—$(C_1-C_6)$ alkyl-;

$R^{11}$ and $R^{12}$ are independently selected from the group consisting of H, $(C_1-C_6)$alkyl and $(C_3-C_{10})$cycloalkyl, or $R^{11}$ and $R^{12}$ together are $C_2-C_6$ alkylene and form a ring with the nitrogen to which they are attached;

$R^{14}$ and $R^{15}$ are independently selected from the group consisting of $(C_1-C_6)$alkyl, halogen, —$NR^{22}R^{23}$, —OH, —$CF_3$, —$OCH_3$, —O-acyl and —$OCF_3$;

$R^{16}$ is $R^{14}$, hydrogen, phenyl, —$NO_2$, —CN, —$CH_2F$, —$CHF_2$, —CHO, —CH=NOR$^{24}$, pyridyl, pyridyl N-oxide, pyrimidinyl, pyrazinyl, —$N(R^{24})$ CONR$^{25}$R$^{26}$, —NHCONH(chloro-$(C_1-C_6)$alkyl), —NHCONH($(C_3-C_{10})$cycloalkyl$(C_1-C_6)$alkyl), —NHCO$(C_1-C_6)$alkyl, —NHCOCF$_3$, —NHSO$_2$N $(R^{22})(R^{23})$, —NHSO$_2(C_1-C_6)$alkyl, —N(SO$_2$CF$_3$)$_2$, —NHCO$_2$—$(C_1-C_6)$alkyl, $C_3-C_{10}$ cycloalkyl, —SR$^{27}$, —SOR$^{27}$, —SO$_2$R$^{27}$, —SO$_2$NH(R$^{22}$), —OSO$_2(C_1-C_6)$alkyl, —OSO$_2$CF$_3$, hydroxy$(C_1-C_6)$ alkyl-, —CON R$^{24}$R$^{25}$, —CON(CH$_2$CH$_2$OCH$_3$)$_2$, —OCONH$(C_1-C_6)$alkyl, —CO$_2$R$^{24}$, —Si(CH$_3$)$_3$ or —B(OC(CH$_3$)$_2$)$_2$;

$R^{17}$ is $(C_1-C_6)$alkyl, —$N(R^{22})(R^{23})$ or $R^{19}$ -phenyl;

$R^{18}$, $R^{22}$, $R^{23}$, $R^{24}$, $R^{25}$ and $R^{26}$ are independently selected from the group consisting of H and $(C_1-C_6)$ alkyl; and $R^{27}$ is $(C_1-C_6)$alkyl or phenyl;

wherein heteroaryl is selected from the group consisting of thienyl, pyridyl and pyrimidyl.

2. A compound of claim 1 wherein Z is CH, and Q and X are each N.

3. A compound of claim 1 wherein $R^1$ is $R^9$-aryl$(C_1-C_6)$ alkyl-, $R^9$-heteroaryl-$(C_1-C_6)$alkyl-, $(C_1-C_6)$alkyl-$SO_2$—, $(C_3-C_6)$cycloalkyl-$SO_2$—, fluoro-$(C_1-C_6)$-alkyl-$SO_2$—, $R^9$-aryl-$SO_2$—, or $R^9$-aryl-NH—C(O)—.

4. A compound of claim 1 wherein $R^2$ is hydrogen and $R^3$ is $(C_1-C_6)$alkyl, $R^9$-aryl, $R^9$-aryl$(C_1-C_6)$-alkyl, $R^9$-heteroaryl, or $R^9$-heteroaryl$(C_1-C_6)$alkyl.

5. A compound of claim 1 wherein R, $R^5$ and $R^7$ are each hydrogen and $R^6$ is —$CH_3$.

6. A compound of claim 1 wherein X is N and $R^4$ is methyl.

7. A compound of claim 1 wherein $R^9$ is H, halogen, $(C_1-C_6)$alkyl or $(C_1-C_6)$alkoxy.

8. A compound of claim 1 wherein $R^8$ is

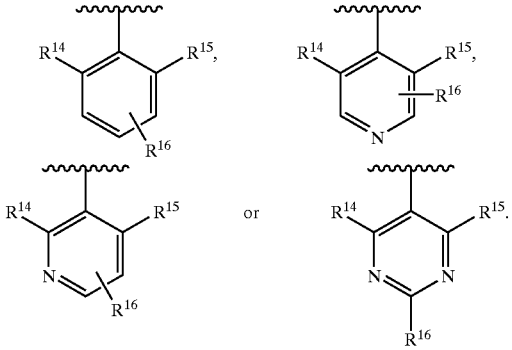

9. A compound of claim 8 wherein $R^{14}$ and $R^{15}$ are independently selected from the group consisting of $(C_1-C_6)$ alkyl, halogen and NH$_2$, and $R^{16}$ is H.

10. A compound of claim 1 selected from the group consisting of compounds of the formula

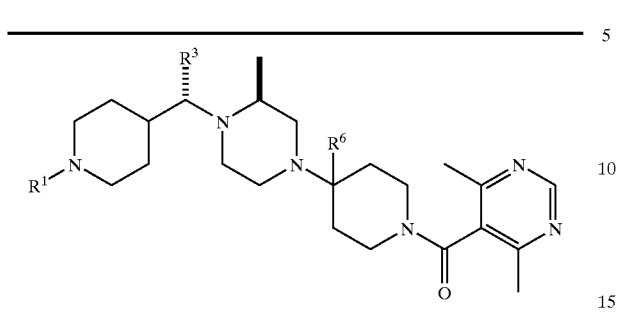

wherein $R^1$ $R^3$ and $R^6$ are as defined in the following table:

| $R^1$ | $R^3$ | $R^6$ |
|---|---|---|
| 4-CH$_3$OC$_6$H$_4$CH$_2$ | C$_6$H$_5$ | CH$_3$ |
| CH$_3$SO$_2$ | C$_6$H$_5$ | CH$_3$ |
| 4-CH$_3$OC$_6$H$_4$CH$_2$ | CH$_2$C$_6$H$_5$ | CH$_3$ |
| CH$_3$SO$_2$ | CH$_2$CH$_2$CH$_3$ | CH$_3$ |
| 4-CH$_3$C$_6$H$_4$SO$_2$ | CH$_2$CH$_2$CH$_3$ | CH$_3$ |
| 4-CH$_3$C$_6$H$_4$SO$_2$ | C$_6$H$_5$ | CH$_3$ |
| C$_6$H$_5$NHC(O) | C$_6$H$_5$ | CH$_3$ |
| 4-CH$_3$OC$_6$H$_4$CH$_2$ | C$_6$H$_5$ | H |
| 4-CH$_3$OC$_6$H$_4$SO$_2$ | C$_6$H$_5$ | CH$_3$ |
| 3-Cl—C$_6$H$_4$SO$_2$ | C$_6$H$_5$ | CH$_3$ |
| CH$_3$SO$_2$ | CH$_2$C$_6$H$_5$ | CH$_3$ |
| 3-Cl—C$_6$H$_4$SO$_2$ | CH$_2$C$_6$H$_5$ | CH$_3$ |
| CH$_3$CH$_2$SO$_2$ | CH$_2$C$_6$H$_5$ | CH$_3$ |
| 4-CH$_3$OC$_6$H$_4$SO$_2$ | 4-F—C$_6$H$_4$ | CH$_3$ |
| CH$_3$SO$_2$ | 4-F—C$_6$H$_4$ | CH$_3$ |
| 3-Cl—C$_6$H$_4$SO$_2$ | 4-F—C$_6$H$_4$ | CH$_3$ |
| CF$_3$C(O) | 4-F—C$_6$H$_4$CH$_2$ | CH$_3$ |
| CH$_3$SO$_2$ | 3-F—C$_6$H$_4$ | CH$_3$ |
| 3-Cl—C$_6$H$_4$SO$_2$ | 3-F—C$_6$H$_4$ | CH$_3$ |
| 4-CH$_3$OC$_6$H$_4$SO$_2$ | 3-F—C$_6$H$_4$ | CH$_3$ |
| CH$_3$SO$_2$ | 4-F—C$_6$H$_4$CH$_2$ | CH$_3$ |
| 3-Cl—C$_6$H$_4$SO$_2$ | 4-F—C$_6$H$_4$CH$_2$ | CH$_3$ |
| 4-CH$_3$OC$_6$H$_4$SO$_2$ | 4-F—C$_6$H$_4$CH$_2$ | CH$_3$ |
| 4-CH$_3$OC$_6$H$_4$CH$_2$ | 2-thienyl | CH$_3$ |
| CF$_3$CH$_2$SO$_2$ | C$_6$H$_5$ | CH$_3$ |
| CF$_3$SO$_2$ | C$_6$H$_5$ | CH$_3$ |
| 4-CH$_3$OC$_6$H$_4$CH$_2$ | 3-thienyl | CH$_3$ |
| 3-Cl—C$_6$H$_4$SO$_2$ | 2-thienyl | CH$_3$ |
| 4-CH$_3$OC$_6$H$_4$SO$_2$ | 2-thienyl | CH$_3$ |
| CH$_3$SO$_2$ | 2-thienyl | CH$_3$ |
| CH$_3$SO$_2$ | 3-thienyl | CH$_3$ |
| 3-Cl—C$_6$H$_4$SO$_2$ | 3-thienyl | CH$_3$ |
| 4-F—C$_6$H$_4$SO$_2$ | CH$_2$C$_6$H$_5$ | CH$_3$ |
| 2-thienyl-SO$_2$ | CH$_2$C$_6$H$_5$ | CH$_3$ |
| C$_6$H$_5$SO$_2$ | CH$_2$C$_6$H$_5$ | CH$_3$ |
| CF$_3$SO$_2$ | CH$_2$C$_6$H$_5$ | CH$_3$ |
| CF$_3$CH$_2$SO$_2$ | CH$_2$C$_6$H$_5$ | CH$_3$ |
| (CH$_3$)$_2$NSO$_2$ | CH$_2$C$_6$H$_5$ | CH$_3$ |
| cyclopropyl-SO$_2$ | 3-F—C$_6$H$_4$ | CH$_3$ |
| 4-F—C$_6$H$_4$SO$_2$ | 3-F—C$_6$H$_4$ | CH$_3$ |
| 4-CH$_3$OC$_6$H$_4$CH$_2$ | n-Butyl | CH$_3$ |
| 3-Cl—C$_6$H$_4$SO$_2$ | n-Butyl | CH$_3$ |
| 4-CH$_3$OC$_6$H$_4$SO$_2$ | n-Butyl | CH$_3$ |
| 3-Cl—C$_6$H$_4$SO$_2$ | 3-pyridyl | CH$_3$ |
| 4-CH$_3$OC$_6$H$_4$SO$_2$ | 3-pyridyl | CH$_3$ |
| 3-Cl—C$_6$H$_4$SO$_2$ | 2-pyridyl | CH$_3$ |
| cyclopropyl-SO$_2$ | C$_6$H$_5$ | CH$_3$ |
| CH$_3$CH$_2$SO$_2$ | C$_6$H$_5$ | CH$_3$ |
| CH$_3$CH$_2$CH$_2$SO$_2$ | C$_6$H$_5$ | CH$_3$ |
| i-propyl-SO$_2$ | C$_6$H$_5$ | CH$_3$ |
| CH$_3$C(O) | C$_6$H$_5$ | CH$_3$ |
| cyclopropyl-C(O) | C$_6$H$_5$ | CH$_3$ |
| CH$_3$CH$_2$C(O) | C$_6$H$_5$ | CH$_3$ |
| i-propyl-C(O) | C$_6$H$_5$ | CH$_3$ |
| 4-CH$_3$OC$_6$H$_4$CH$_2$ | 3,5-difluorophenyl | CH$_3$ |
| cyclopropyl-SO$_2$ | 3,5-difluorophenyl | CH$_3$ |
| CH$_3$SO$_2$ | cyclohexyl | CH$_3$ |

11. A compound of claim 1 selected from the group consisting of

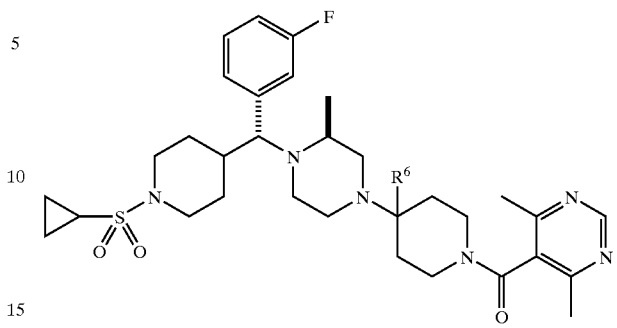

and

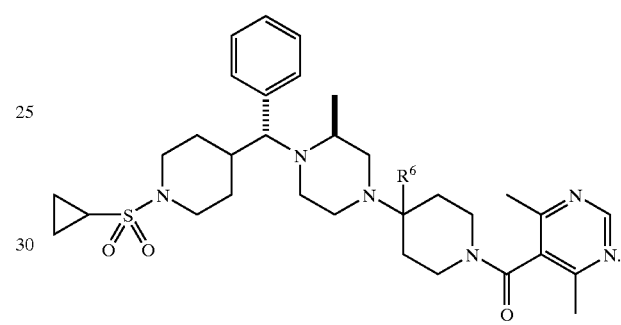

12. A pharmaceutical composition comprising an effective amount of a compound of claim 1 in combination with a pharmaceutically acceptable carrier.

13. A method of treating Human Immuno-deficiency Virus comprising administering to a mammal in need of such treatment an effective amount of a compound of claim 1.

14. The compound of the formula

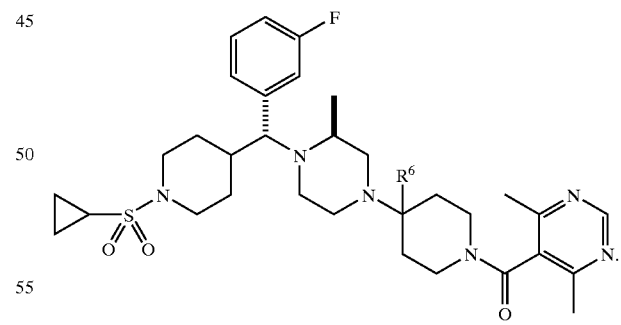

15. A pharmaceutical composition comprising an effective amount of a compound of claim 14 in combination with a pharmaceutically acceptable carrier.

16. A method of treating Human Immuno-deficiency Virus comprising administering to a mammal in need of such treatment an effective amount of a compound of claim 14.

* * * * *